United States Patent
Row et al.

(10) Patent No.: US 11,786,691 B2
(45) Date of Patent: *Oct. 17, 2023

(54) ELECTRICAL HEATER WITH PARTICULAR APPLICATION TO HUMIDIFICATION AND FLUID WARMING

(71) Applicant: ResMed Pty Ltd, Bella Vista (AU)

(72) Inventors: Nathan John Row, Sydney (AU); Ronald James Huby, Sydney (AU); Alexander Virr, Gosford (AU)

(73) Assignee: ResMed Pty Ltd, Bella Vista (AU)

( * ) Notice: Subject to any disclaimer, the term of this patent is extended or adjusted under 35 U.S.C. 154(b) by 521 days.

This patent is subject to a terminal disclaimer.

(21) Appl. No.: 15/973,719

(22) Filed: May 8, 2018

(65) Prior Publication Data

US 2018/0250491 A1    Sep. 6, 2018

Related U.S. Application Data

(63) Continuation of application No. 14/464,765, filed on Aug. 21, 2014, now Pat. No. 9,993,609, which is a (Continued)

(30) Foreign Application Priority Data

Jun. 5, 2007 (AU) ............................... 2007902992
Jul. 4, 2007 (AU) ............................... 2007903599

(51) Int. Cl.
*A61M 16/16* (2006.01)
*A61M 16/10* (2006.01)
(Continued)

(52) U.S. Cl.
CPC ........ *A61M 16/162* (2013.01); *A61M 16/109* (2014.02); *A61M 16/1075* (2013.01);
(Continued)

(58) Field of Classification Search
CPC .............. A61M 16/162; A61M 16/109; A61M 16/1075; A61M 16/16; A61M 2205/3368;
(Continued)

(56) References Cited

U.S. PATENT DOCUMENTS 1,062,344 A    5/1913   Mann
1,839,156 A    12/1931  Lumpkin
(Continued)

FOREIGN PATENT DOCUMENTS

CN    1202602 A    12/1998
CN    1963321 A    5/2007
(Continued)

OTHER PUBLICATIONS

Mar. 7, 2013 International Search Report issued in PCT/EP2012/071739.
(Continued)

*Primary Examiner* — Timothy A Stanis
*Assistant Examiner* — Matthew R Moon
(74) *Attorney, Agent, or Firm* — Nixon & Vanderhye P.C.

(57) ABSTRACT

A humidifier tub for a respiratory apparatus is configured to deliver pressurized breathable gas to a patient's airways. The humidifier tub includes a base and a side wall defining a reservoir for containing a supply of liquid to be evaporated. In addition, the container is made of a first material. The humidifier tub also includes a heating element provided inside the container and covered by a layer. The layer includes a second material different from the first material.

24 Claims, 20 Drawing Sheets

Related U.S. Application Data continuation of application No. 12/600,770, filed as application No. PCT/AU2008/000799 on Jun. 3, 2008, now Pat. No. 8,873,941.

(60) Provisional application No. 60/986,404, filed on Nov. 8, 2007.

(51) Int. Cl.
| | |
|---|---|
| *H05B 3/48* | (2006.01) |
| *G01F 23/24* | (2006.01) |
| *H05B 3/46* | (2006.01) |
| *G01F 23/22* | (2006.01) |
| *G01R 19/00* | (2006.01) |

(52) U.S. Cl.
CPC .............. *A61M 16/16* (2013.01); *G01F 23/22* (2013.01); *G01F 23/24* (2013.01); *G01F 23/241* (2013.01); *G01R 19/0092* (2013.01); *H05B 3/46* (2013.01); *H05B 3/48* (2013.01); *A61M 16/161* (2014.02); *A61M 2205/3368* (2013.01); *A61M 2205/3379* (2013.01); *A61M 2205/3382* (2013.01); *A61M 2205/3386* (2013.01); *A61M 2205/3389* (2013.01); *A61M 2209/02* (2013.01)

(58) Field of Classification Search
CPC ........ A61M 16/161; A61M 2205/3379; A61M 2209/02; A61M 2205/3382; A61M 2205/3386; A61M 2205/3389; G01F 23/22; G01F 23/24; G01F 23/241; G01R 19/0092; H05B 3/48; H05B 3/46; B29C 39/10; B29C 45/14; B29C 45/14639; B29C 45/14819; B29C 70/68; B29C 70/70; Y10T 29/4998; Y10T 29/49982; Y10T 29/49984
USPC ..... 264/104, 255, 279, 279.1; 219/420–424; 392/458
See application file for complete search history.

(56) References Cited

U.S. PATENT DOCUMENTS

| | | | |
|---|---|---|---|
| 3,672,568 A | 6/1972 | Foote | |
| 3,694,622 A * | 9/1972 | Bentley | H05B 3/146 |
| | | | 219/213 |
| 3,809,374 A | 5/1974 | Schossow | |
| 3,937,920 A | 2/1976 | Gundacker et al. | |
| 4,155,001 A | 5/1979 | Schossow | |
| 4,222,971 A | 9/1980 | Eilert | |
| 4,225,542 A * | 9/1980 | Wall | A61M 16/1075 |
| | | | 261/DIG. 65 |
| 4,284,878 A * | 8/1981 | Bartels | G01F 23/22 |
| | | | 340/622 |
| 4,658,448 A | 4/1987 | Rogers | |
| 4,801,782 A | 1/1989 | Ineson | |
| 4,980,539 A | 12/1990 | Walton | |
| 5,031,612 A | 7/1991 | Clementi | |
| 5,243,973 A | 9/1993 | Falb et al. | |
| 5,432,322 A | 7/1995 | Ingram et al. | |
| 5,522,523 A | 6/1996 | Nogles | |
| 5,546,926 A | 8/1996 | Lake | |
| 5,598,502 A | 1/1997 | Takahasi | |
| 5,673,687 A | 10/1997 | Dobson | |
| 5,693,244 A | 12/1997 | Pragt | |
| 5,752,498 A | 5/1998 | Lake et al. | |
| 6,000,224 A | 12/1999 | Foye | |
| 6,135,427 A | 10/2000 | Tsai | |
| 6,163,248 A * | 12/2000 | Paek | F21V 33/0036 |
| | | | 340/321 |
| 6,263,158 B1 | 7/2001 | Rutherford | |
| 6,392,206 B1 | 5/2002 | Von Arx | |
| 6,433,317 B1 | 8/2002 | Arx | |
| 6,670,583 B2 | 12/2003 | Kara | |
| 6,674,052 B1 | 1/2004 | Luo | |
| 6,704,497 B2 | 3/2004 | Bikhovsky | |
| 6,810,732 B2 | 11/2004 | Shon | |
| 6,870,135 B2 | 3/2005 | Hamm | |
| 7,049,558 B2 * | 5/2006 | Baer | B01J 19/0093 |
| | | | 219/548 |
| 7,068,924 B2 | 6/2006 | Watanabe | |
| 7,159,618 B2 | 1/2007 | Broyer et al. | |
| 7,182,017 B1 * | 2/2007 | Knepler | A47J 31/467 |
| | | | 340/618 |
| 7,305,178 B2 | 12/2007 | Haubold | |
| 7,308,193 B2 | 12/2007 | Halsall | |
| 7,389,688 B1 | 6/2008 | Vander Horst | |
| 7,413,173 B2 | 8/2008 | DiMatteo | |
| 7,826,725 B2 | 11/2010 | Wolff | |
| 8,810,260 B1 | 8/2014 | Zhou | |
| 8,873,941 B2 | 10/2014 | Row et al. | |
| 10,317,098 B2 * | 6/2019 | Bayer | A61M 16/161 |
| 2002/0013578 A1 | 1/2002 | Clement | |
| 2002/0163090 A1 | 11/2002 | Chu | |
| 2003/0001117 A1 | 1/2003 | Shon | |
| 2003/0010117 A1 | 1/2003 | Shon | |
| 2003/0041604 A1 | 3/2003 | Jang | |
| 2003/0132535 A1 | 7/2003 | Lipscombe et al. | |
| 2004/0155020 A1 | 8/2004 | Worrell et al. | |
| 2004/0182849 A1 * | 9/2004 | Shozo | F24C 15/003 |
| | | | 219/403 |
| 2004/0221843 A1 | 11/2004 | Baecke | |
| 2005/0150491 A1 | 7/2005 | Chen | |
| 2005/0248044 A1 | 11/2005 | Kim | |
| 2006/0180223 A1 | 8/2006 | Broyer et al. | |
| 2007/0104469 A1 | 5/2007 | Kang | |
| 2007/0125376 A1 | 6/2007 | Reinstadtler | |
| 2007/0152356 A1 | 7/2007 | Huang | |
| 2008/0072900 A1 | 3/2008 | Kenyon et al. | |
| 2008/0073802 A1 | 3/2008 | Anderson | |
| 2008/0185742 A1 | 8/2008 | Novotny | |
| 2008/0245365 A1 | 10/2008 | Genger et al. | |
| 2008/0257346 A1 | 10/2008 | Lathrop et al. | |
| 2009/0000620 A1 | 1/2009 | Virr | |
| 2009/0007797 A1 * | 1/2009 | Ando | A21B 3/04 |
| | | | 99/330 |
| 2009/0320840 A1 | 12/2009 | Klasek et al. | |
| 2010/0132708 A1 | 6/2010 | Martin et al. | |
| 2010/0147299 A1 | 6/2010 | Row et al. | |
| 2011/0017212 A1 | 1/2011 | Kenyon et al. | |
| 2011/0023874 A1 | 2/2011 | Bath et al. | |
| 2011/0155132 A1 | 6/2011 | Virr et al. | |
| 2013/0008440 A1 | 1/2013 | Maurer et al. | |
| 2014/0131904 A1 | 5/2014 | Tang et al. | |
| 2014/0352694 A1 | 12/2014 | Row et al. | |
| 2015/0115483 A1 | 4/2015 | Miller | |
| 2015/0202402 A1 | 7/2015 | Kat | |
| 2019/0390863 A1 * | 12/2019 | Bayer | A61M 16/16 |

FOREIGN PATENT DOCUMENTS

| | | |
|---|---|---|
| EP | 1 369 141 A1 | 12/2003 |
| FR | 2 856 046 A1 | 12/2004 |
| GB | 2 327 028 A | 1/1999 |
| JP | 55-38578 | 10/1980 |
| JP | 56-6908 | 2/1981 |
| JP | 57-501308 | 7/1982 |
| JP | 59-68229 | 5/1984 |
| JP | 61-33361 | 9/1986 |
| JP | 64-500088 | 1/1989 |
| JP | 3-115930 | 5/1991 |
| JP | 8-189212 A | 7/1996 |
| JP | 10-234621 A | 9/1998 |
| JP | 10-312705 A | 11/1998 |
| JP | 2000-28201 A | 1/2000 |
| JP | 2003-57092 | 2/2003 |
| JP | 2005-506157 | 3/2005 |
| JP | 2005-538802 | 12/2005 |
| JP | 2006-151200 A | 6/2006 |

(56) References Cited

FOREIGN PATENT DOCUMENTS

| | | |
|---|---|---|
| JP | 2006-158969 | 6/2006 |
| JP | 2006-527825 A | 12/2006 |
| JP | 2007-26989 A | 2/2007 |
| JP | 2010-529400 | 8/2010 |
| WO | WO 82/00935 A1 | 3/1982 |
| WO | 88/00068 | 1/1988 |
| WO | WO 97/39667 A1 | 10/1997 |
| WO | 02/13578 A1 | 2/2002 |
| WO | WO 02/13578 A1 | 2/2002 |
| WO | 2004/026382 | 4/2004 |
| WO | WO 2006/012878 A1 | 2/2006 |
| WO | WO 2007/019626 A1 | 2/2007 |
| WO | 2008/148154 A1 | 12/2008 |
| WO | WO 2008/148154 | 12/2008 |
| WO | WO 2010/031126 | 3/2010 |
| WO | WO 2012/171072 | 12/2012 |

OTHER PUBLICATIONS

Mar. 7, 2013 Written Opinion issued in PCT/EP2012/071739.
Sep. 25, 2014 International Preliminary Report on Patentability issued in PCT/EP2012/071739.
Apr. 21, 2015 First Examination Report issued in New Zealand Application No. 629805.
Jan. 17, 2017 European Examination Report issued in EP Application No. 12791708.6.
Mar. 23, 2017 Office Action issued in U.S. Appl. No. 14/384,639.
Jun. 23, 2017 Amendment filed in U.S. Appl. No. 14/384,639.
Sep. 21, 2017 Office Action issued in U.S. Appl. No. 14/384,639.
Sep. 25, 2017 First Examination Report issued in related New Zealand Application No. 734898.
Jan. 19, 2018 Amendment filed in U.S. Appl. No. 14/384,639.
Mar. 9, 2018 Office Action issued in U.S. Appl. No. 14/384,639.
Apr. 27, 2018 Further Examination Report issued in New Zealand Application No. 734898.
Jun. 29, 2018 Amendment filed in U.S. Appl. No. 14/384,639.
Nov. 1, 2018 Office Action issued in U.S. Appl. No. 14/384,639.
Summons to Attend Oral Proceedings Pursuant to Rule 115(1) EPC, issued in EP Application No. 12791708.6, six pages, mailed Jan. 2, 2019.
Jan. 16, 2019 Amendment filed in U.S. Appl. No. 14/384,639.
Jan. 31, 2019 Notice of Allowance issued in U.S. Appl. No. 14/384,639.
Communication dated May 10, 2019 issued in European Application No. 08756887.9 (6 pages).
Office Action dated Dec. 20, 2016 issued in European Application No. 08756887.9 (7 pages).
Notice of Reasons for Rejection dated Oct. 31, 2016 issued in Japanese Application No. 2014-250841 with English translation (6 pages).
First Examination Report dated Nov. 2, 2016 issued in Australian Application No. 2015201748 (5 pages).
First Examination Report dated Jul. 26, 2016 issued in New Zealand Application No. 722026 (2 pages).
Notification of the Second Office Action dated Aug. 31, 2016 issued in Chinese Application No. 201510221847.7 with English translation (7 pages).
Notice of Reasons for Rejection dated Feb. 15, 2016 issued in Japanese Application No. 2014-250841 with English translation (9 pages).
Notification of the First Office Action dated Dec. 21, 2015 issued in Chinese Application No. 201510221847.7 with English language translation (14 pages).
Notice of Reasons for Rejection dated Nov. 30, 2015 issued in Japanese Application No. 2010-510611 with English language translation (17 pages).
Notice of Reasons for Rejection dated Nov. 30, 2015 issued in Japanese Application No. 2012-239969 with English language translation (23 pages).
Notification of Reexamination dated Oct. 14, 2014 issued in Chinese Application No. 200880019079.5 with English translation (19 pages).
Peng, Yao, et al., "Electrically Heating Device", Liaoning Science & Technology Publishing House, First Edition, Sep. 1991 (4 pages).
Decision of Rejection dated Aug. 18, 2014 in Japanese Application No. 2010-510611 with English translation (2 pages).
Decision to Reject the Amendments dated Aug. 18, 2014 in Japanese Application No. 2010-510611 with English translation (7 pages).
Decision of Rejection dated Aug. 11, 2014 in Japanese Application No. 2012-239969 with English translation (6 pages).
International Search Report (Corrected Version) dated Aug. 26, 2008 in PCT/AU2008/000799.
International Preliminary Report on Patentability dated Dec. 7, 2009 in PCT/AU2008/000799.
Examination Report dated Apr. 27, 2011 in New Zealand Application No. 581141 (3 pages).
Extended European Search Report dated Jun. 8, 2011 in European Application No. 08756887.9 (7 pages).
Chinese Office Action dated Mar. 5, 2012 in Chinese Appln. No. 200880019079.5, with English translation (16 pages).
Examination Report dated May 23, 2012 in New Zealand Appln. No. 581141 (2 pages).
Notice of Reasons for Rejection dated Jul. 31, 2012 in Japanese Application No. 2010-510611, with English translation (5 pages).
Patent Examination Report No. 1 dated Dec. 12, 2012 in Australian Application No. 2008258265 (5 pages).
Notification of the Second Office Action dated Nov. 13, 2012 in Chinese Application No. 200880019079.5, with English Translation (19 pages).
Notice of Reasons for Rejection dated Apr. 2, 2013 in Japanese Application No. 2010-510611, with English Translation (8 pages).
Decision of Rejection dated Jun. 4, 2013 in Chinese Application No. 200880019079.5, with English Translation (19 pages).
Patent Examination Report No. 2 dated Sep. 9, 2013 in Australian Application No. 2008258265 (3 pages).
Notice of Reasons for Rejection dated Nov. 19, 2013 in Japanese Application No. 2012-239969, with English Translation (8 pages).
Notice of Reasons for Rejection dated Jan. 7, 2014 in Japanese Application No. 2010-510611, with English translation (8 pages).
Extended European Search Report dated Sep. 13, 2021 issued in European Application No. 21157223.5 (10 pages).
Office Action dated Sep. 13, 2022 issued in U.S. Appl. No. 16/432,513 (17 pages).

\* cited by examiner

ELECTRICAL HEATER WITH PARTICULAR APPLICATION TO HUMIDIFICATION AND FLUID WARMING

CROSS REFERENCE TO RELATED APPLICATIONS

This application is a continuation of U.S. application Ser. No. 14/464,765, filed Aug. 21, 2014, now allowed, which is a continuation of U.S. application Ser. No. 12/600,770, filed Nov. 18, 2009, now U.S. Pat. No. 8,873,941, which is the U.S. national phase of International Application No. PCT/AU2008/000799 filed Jun. 3, 2008 which designated the U.S. and claims priority to Australian Provisional Applications 2007902992, filed Jun. 5, 2007, and 2007903599, filed Jul. 4, 2007 and U.S. Provisional Application 60/986,404, filed Nov. 8, 2007, the entire contents of these applications being incorporated herein by reference in their entirety.

FIELD OF THE INVENTION

The present invention relates generally to electrical heaters and particularly to integrated electric heaters for use in heating fluids. More particularly, the present invention relates to in-molded heaters for heating fluids within containers. The electrical heater may be used in a range of devices including, for example, humidification devices, electric jugs, other fluid warming containers, fans and the like. The heater may be used in a respiratory humidification device.

BACKGROUND OF THE INVENTION

Respiratory apparatus commonly have devices to alter the humidity of the breathable gas in order to reduce drying of the patient's airway and consequent patient discomfort and associated complications. The use of a humidifier placed between the positive airway pressure (PAP) device and the patient mask produces humidified gas that minimizes drying of the nasal mucosa and increases patient airway comfort.

Many humidifier types have been proposed, including humidifiers that are either integrated with, or configured to be coupled to, the respiratory apparatus. Independent humidifiers have also been proposed. While passive humidifiers can provide some relief, generally a heated humidifier is required to provide sufficient humidity and temperature to the air so that the patient will be comfortable.

Humidifiers typically comprise a water tub having a capacity of several hundred millilitres, a heating element for heating the water in the tub, a control to enable the level of humidification to be varied, a gas inlet to receive gas from the PAP device, and a gas outlet adapted to be connected to a gas conduit that delivers the humidified, pressurized flow of breathable gas to the patient's mask.

Commonly, humidifier tubs are attached either directly to a humidifier control base or to a system base, or cradle, that facilitates the correct assembly of the PAP device with the humidifier. Generally, the humidifier control base or the system base, or cradle, comprises a heating plate that contacts the base of the humidifier tub to facilitate heating of the water within the humidifier tub.

FIG. 1 depicts a prior art humidifier device 10 with a control base 16, which comprises a heater plate 18. A water tub 12 comprising an air inlet 20, an air outlet 22 and a heat conductive tub base 14, is adapted to sit upon the heater plate 18 of the control base 16. The base systems typically comprise a spring loaded heater plate 18 on to which the water tub 12 is attached. The spring loaded heater plate 18 ensures good thermal contact with the tub base 14 of the water tub 12, although some thermal losses occur between the heater plate 18 and the water tub 12. For example, the Fisher & Paykel HC200™ system and the Respironics RemStar™ heated humidifier have spring loaded heater plates. However, such spring loaded heater plates can provide a friction force against insertion of the water tub, which may make installation of the water tub difficult for some users, especially older or frail users.

The water in the water tub 12 is heated via thermal conduction between the heater plate 18 and the tub base 14 of the water tub 12. The tub base 14 is commonly formed of aluminium or stainless steel. The tub base 14 is generally formed as a separate component of the water tub 12 and sealingly coupled to the upper portion of the water tub, for example using adhesives or a stamped rolled edge. For example, see Applicant's WO 2007/019626 A1, the entire contents of which are incorporated by reference. This results in multiple components that require assembly during manufacture of the humidifier and increase the size and weight of the device. Furthermore, the assembled construction provides an increased risk of leakage between the sealed components.

Other forms of heaters are known but have rarely, or not at all, been used in commercially available respiratory humidifiers to date. One example is induction heaters as described in Applicant's WO 2007/101298 A1, the entire contents of which are incorporated by reference. Flexible layered heaters are also known and have been used in a range of applications including defogging mirrors, screens for televisions, video cameras & mobile phones and blanket heaters. For example, printed thick film heating elements that comprise conductive and resistive inks, such as carbon ink or silver ink, have been used. FIG. 2 shows the general construction of a printed thick film heating element 28 comprising a first film substrate layer 30 with a conductive and resistive inks layer 34 printed thereon and then a second film 32. The two films 30, 32 are laminated together with a pressure sensitive adhesive sandwiching the ink layer 34. The films are typically thermoplastic or thermoset polymers such as polyester or polyimide. Such flexible layered heaters may be attached to the required surfaces to provide the required heating function.

Many products are provided with labels attached to their surfaces. Labels are commonly used to provide decorative designs, branding, texture, instructions, warnings and other such graphical material to products. There are many different forms of product labels and techniques for attaching such labels to objects. In-mold labeling is a method used to attach the labels to the surface of a molded object wherein the label is attached within the wall of a molded object. In-mold labeling is used with blow molded and injection molded products such as toys, containers for cleaning products, motor oil, beverages and the like. The label is printed onto a film using known printing techniques such as flexography, offset, screen or hot stamping printing. U.S. Pat. No. 6,551,671 (Nishizawa et al.) describes a process for in-mold labeling.

FIG. 3 illustrates the general construction of an in-mold label 35 where a graphic 38 is printed upon a film 36. The formed printed film 36, 38 is placed and held within an open mold with the film 36 surface adjacent to the mold. The mold is closed and the hot mold resin 40, such as a plastic polymer, is extruded or injected into the mold to form the desired object shape with an integrally molded label. The film 36 is generally comprised of a polypropylene or polyethylene copolymer that comprises a heat-activated adhesive that facilitates attachment of the printed film within the wall of the molded object.

Conventional humidifiers have the disadvantage of many different components that require assembly and increase weight. The assembly of different components and the use of heater plates and tubs with conductive base plates provides an increased risk of water leakage. The present invention seeks to address one or more of these disadvantages or at least provide a reasonable alternative.

SUMMARY OF THE INVENTION

An aspect of the invention is directed to a heater element that provides safe and effective heat. Another aspect of the invention provides a heater element that is molded within a container during manufacture. A further aspect relates to an in-mold heater element comprising a polymer film having electrically conductive ink printed upon at least one surface. In another aspect the electrically conductive ink is carbon and/or silver ink. In a further aspect the polymer film is a polyester, polyimide, polycarbonate or polypropylene.

Another aspect is related to a heater element comprising a polymer film having an electrically conductive ink printed upon at least one surface wherein the polymer film is molded into at last one surface of the molded object. In an additional aspect, the heater element comprises electrical connectors fastened to the electrically conductive ink to provide power and/or control signals. In a further aspect, the heater element comprises sensors such as a temperature sensor for controlling the temperature of the heater element. Yet another aspect includes a thermal fuse to provide a protection system to protect against over heating of the heater element.

Another aspect of the invention relates to a method for manufacturing an object comprising an in-molded heater element. In a further aspect the object is formed by injection molding. In an alternative aspect the object is formed by extrusion molding.

Another aspect of the invention relates to a method for manufacturing a humidifier comprising an in-mold heater element. In a further aspect the humidifier has a reduced number of parts and/or simple assembly process.

Yet another aspect of the invention relates to a respiratory humidifier comprising a heater formed from an in-mold heater element.

Still another aspect of the invention relates to an electrical heater having simple electrical connections.

According to one sample embodiment of the invention, a heater element comprises a first polymer film having an electrically conductive circuit provided upon a surface. The first polymer film is electrically insulating and is molded into at least one surface of a molded object.

According to another sample embodiment of the invention, a method of manufacturing an in-mold heater element comprises i) providing an electrically conductive circuit on a first surface of a first polymer film; ii) placing the first polymer film including the electrically conductive circuit in a mold such that a second surface of the first polymer film opposite the first surface is adjacent the mold; and iii) insert molding resin to form a predetermined molded shape such that the first polymer film is incorporated within at least one surface of the molded shape.

According to a further sample embodiment of the invention, a humidifier comprises a tub configured to contain a supply of water; and a heater comprising a first polymer film having an electrically conductive circuit provided upon a surface. The first polymer film is electrically insulating and the tub is formed of molded resin and the heater is molded at least partially within the resin.

According to a still further sample embodiment of the invention, a method of humidifying a flow of pressurized breathable gas comprises passing the flow of pressurized breathable gas over a supply of water contained in a tub, wherein the tub is formed of molded resin and a heater comprising a first polymer film having an electrically conductive circuit on a first surface is molded at least partially within the resin.

According to yet another sample embodiment of the invention, a molded object comprises a heater element, the heater element comprising a first polymer film having an electrically conductive circuit upon a surface. The first polymer film is molded into at least one surface of the molded object. A control system configured to control a temperature of the heater element.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

Sample embodiments of the present invention will be described in relation to the attached drawings, in which:

FIG. 9b schematically illustrates a cross-section through A-A of the mating arrangement of FIG. 9a;

DETAILED DESCRIPTION OF ILLUSTRATED EMBODIMENTS

Heater Element First Embodiment

Figure 1:
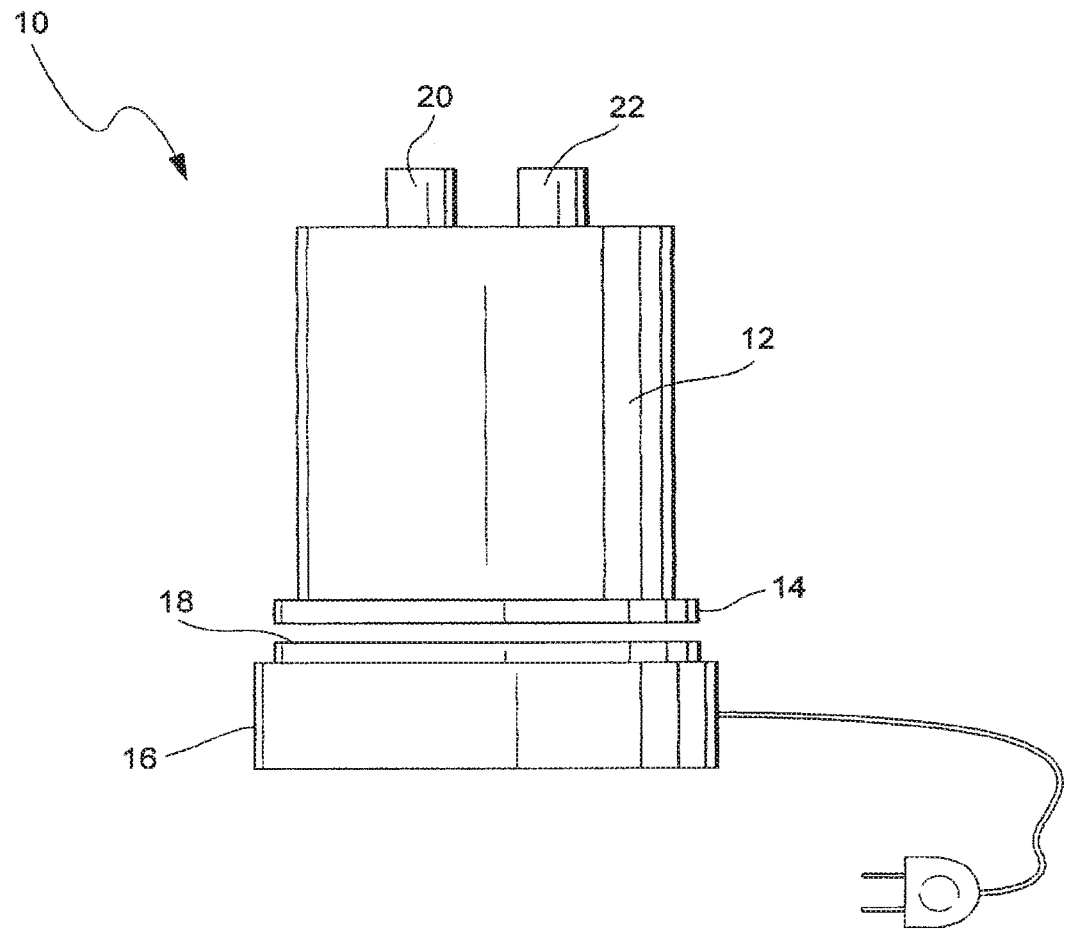
FIG. 1 schematically illustrates a prior art humidifier device.
Figure 2:
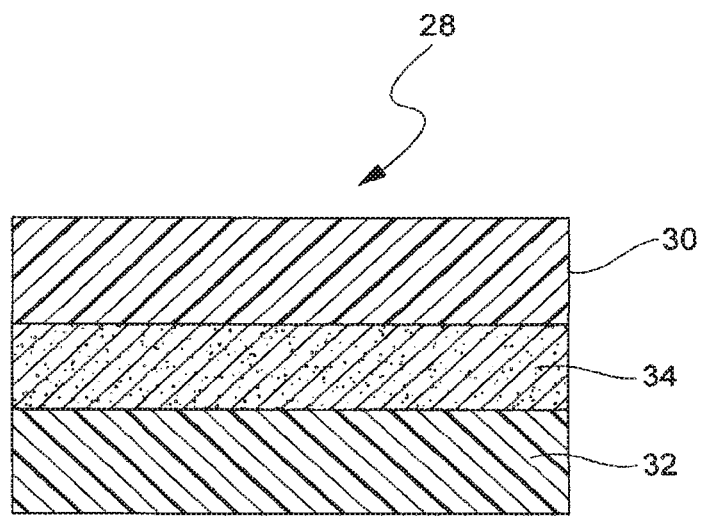
FIG. 2 schematically illustrates a thick film carbon heater according to the prior art.
Figure 3:
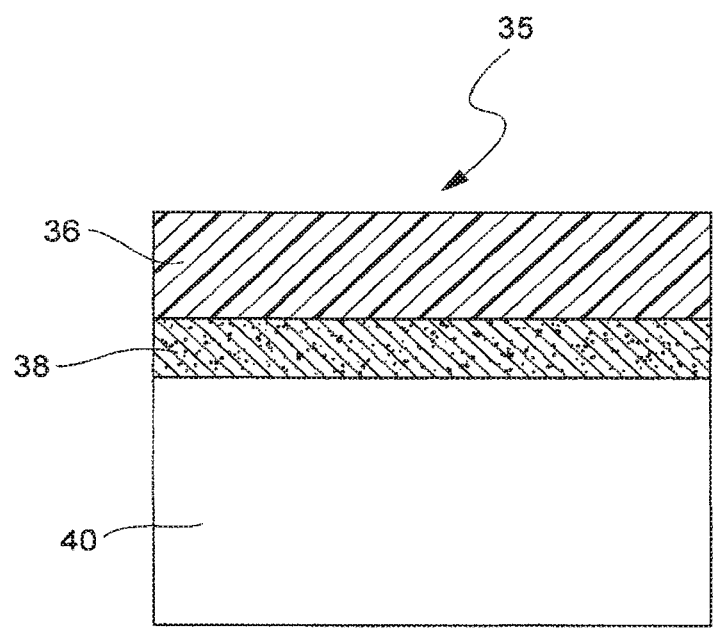
FIG. 3 schematically illustrates an in-mold label according to the prior art.
Figure 4A:
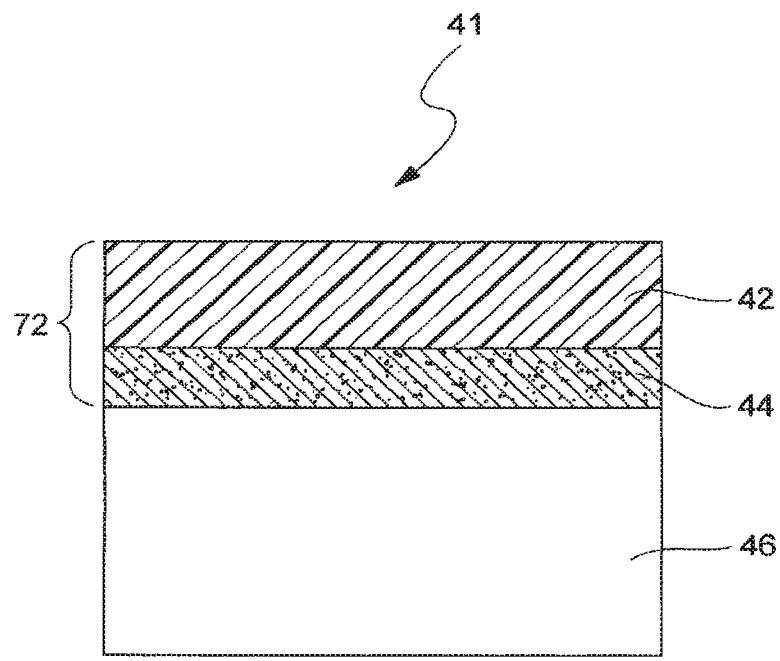
FIG. 4a schematically illustrates an in-mold thick film carbon heater according to a sample embodiment of the invention.

FIG. 4a illustrates the general construction of an in-mold heater element 41 formed according a method of the invention. A conductive ink 44, such as carbon ink or silver ink, is printed upon the surface of a film 42. The combined printed film and heater element 72 is then placed within an open mold with the film 42 adjacent the mold. The mold is closed and mold resin 46 is injected or extruded into the closed mold to form the desired object. The resulting molded object has a printed film heater element 72 molded within the wall of the object.

In one embodiment the film 42 is a thermoplastic or thermoset polymer material such as polyester, polyimide, polycarbonate, polypropylene or other polymers that provide good thermal conductivity together with electrical insulation properties and mechanical protection of the printed ink. The film is thick enough to provide a stable film for the printed ink while still providing sufficient heat transfer. The film may have a thickness between 0.01 mm to 1 mm, for example between 0.05 mm to 0.5 mm.

Heater Element Second Embodiment

Figure 4B:
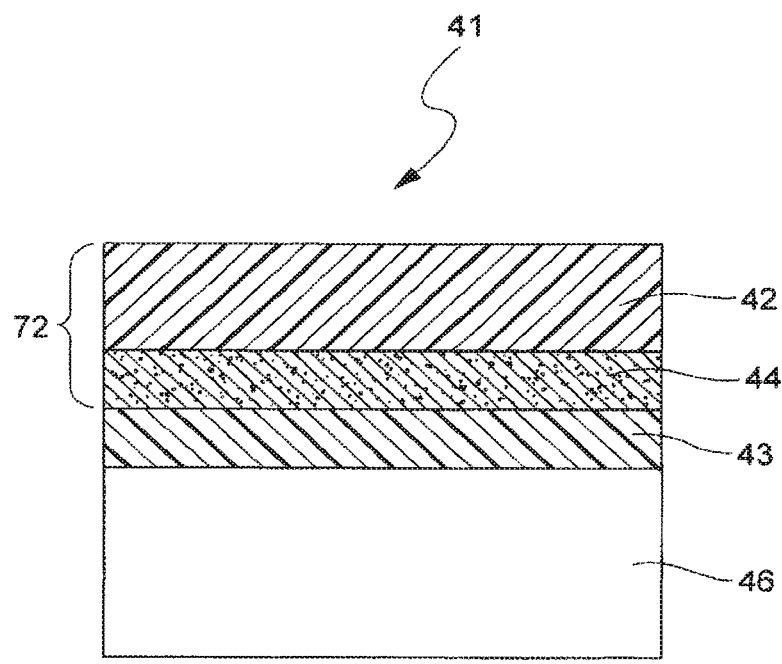
FIG. 4b schematically illustrates an in-mold thick film carbon heater according to a sample embodiment of the invention.

In a further sample embodiment shown in FIG. 4b, a second film 43 may be used to sandwich the conductive ink 44 to provide a protective layer between the conductive ink 44 and the molding resin 46. The second film 43 may also be formed from a thermoplastic or thermoset polymer material. The second film 43 may be electrically insulating, similarly to the film 42. Alternatively, the second film 43 may be resistive or conductive as described in more detail below.

Heater Element Third Embodiment

Figure 4C:
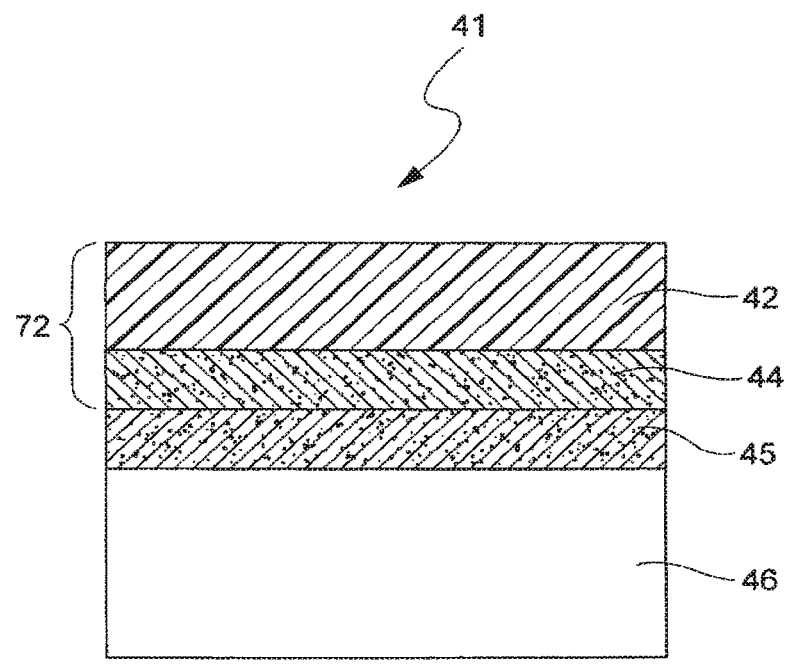
FIG. 4c schematically illustrates an in-mold thick film carbon heater according to a sample embodiment of the invention.

In another sample embodiment shown in FIG. 4c, a second layer 45 of protective ink is printed over the conductive ink 44 to provide a protective layer.

The electrically conductive ink may be carbon ink or silver ink or any other suitably electrically conductive ink. The conductive ink is generally printed in a thickness of about 5 μm to 40 μm, for example about 10 μm to 25 μm. However, larger or smaller conductive ink thicknesses are considered within the scope of the invention. In a sample embodiment, the electrically conductive ink is printed on to the film using a screen printing process. However, it should be appreciated that other printing processes may be used, for example etching.

The pattern of the conductive ink affects the distribution of the heat and the resistance in the circuits. The pattern of the electrically conductive ink applied to the film may be adjusted to provide different power densities. The thickness, width, length, and material properties (resistivity/conductivity) of the electrically conductive ink pattern determines the resistance in the circuit. A thicker or wider ink pattern has lower resistance than thinner or narrow ink patterns, whereas the resistance increases with increasing lengths of the conductive ink pattern.

Heater Element Fourth Embodiment

In a sample embodiment, the ink pattern is designed to provide a given resistance to allow a particular voltage to be applied to the circuit. For example, the electrically conductive ink may be applied in a series of parallel bands linked with a perpendicular band, for example at bands periphery, or the ink may be applied as a single continuous circuit.

Figure 4D:
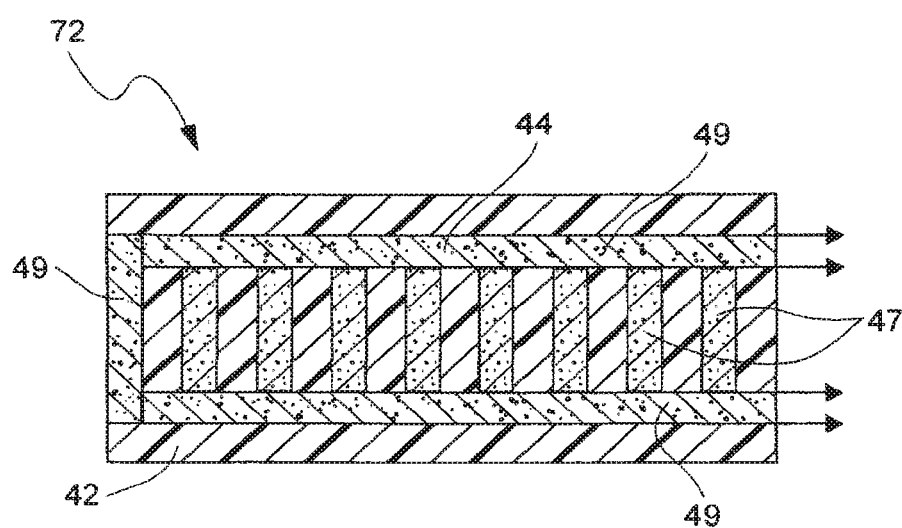
FIG. 4d schematically illustrates a sample embodiment of a conductive ink pattern having parallel bands.

FIG. 4d illustrates an ink pattern having a series of linked parallel bands. The arrows represent the electrical connections that are made to the ends of the circuit. It is to be understood that this is only a sample and other ink patterns are considered within the scope of the invention.

The conductive ink circuits may include a combination of conductive inks such as carbon and silver ink to provide different resistance properties within the heating element. Carbon ink has a much higher resistance compared to silver ink. For example, carbon ink 47 may be used to form the series of parallel bands, as shown in FIG. 4d, and silver ink 49 may be used to link the carbon ink bands 47 at their periphery.

Heater Element Fifth Embodiment

Figure 4E:
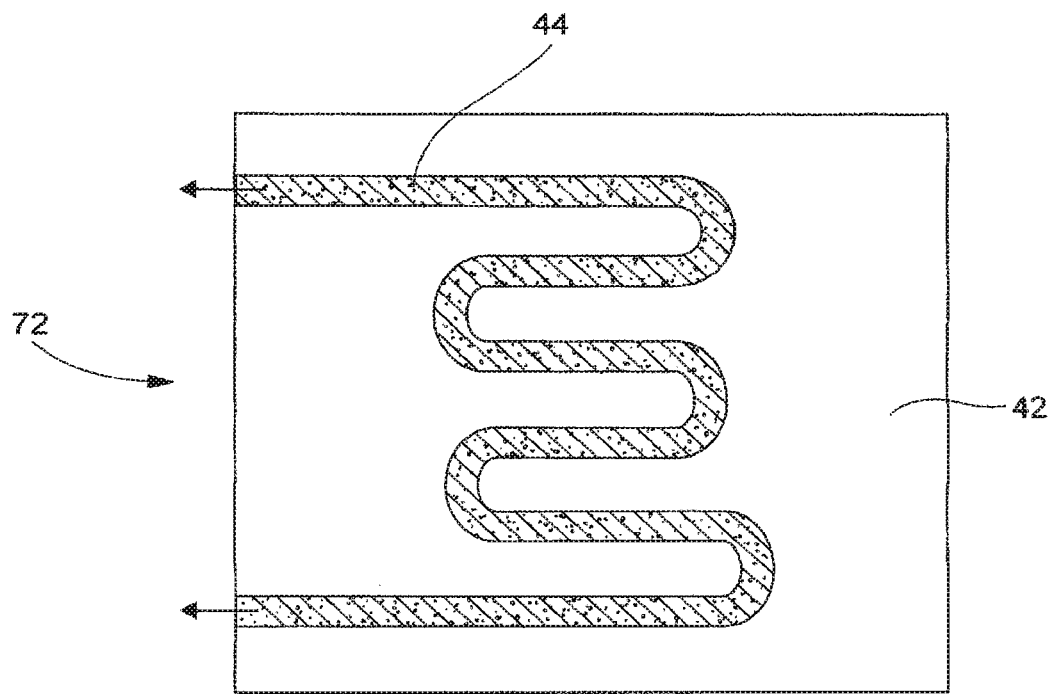
FIG. 4e schematically illustrates a sample embodiment of a conductive ink pattern having a single continuous circuit.

FIG. 4e illustrates an ink pattern having a single continuous circuit. As in FIG. 4d, the arrows represent the electrical connections that are made to the ends of the circuit. It is also to be understood that this is only a sample of a continuous circuit and other ink continuous patterns are considered within the scope of the invention.

Heater Element Sixth Embodiment

Figure 4F:
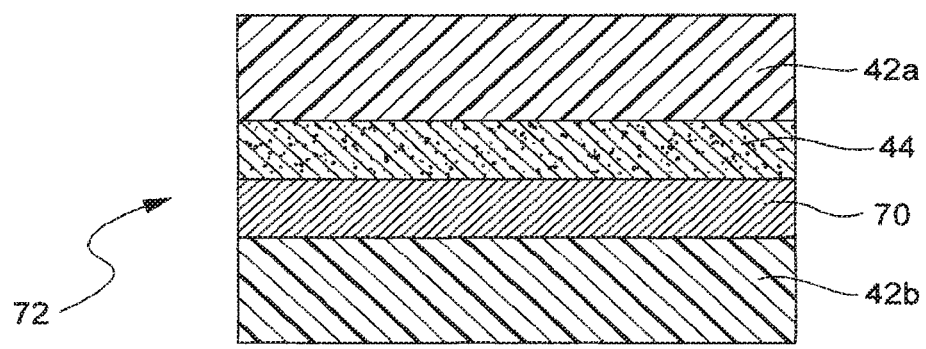
FIG. 4f schematically illustrates a heater element according to a sample embodiment of the invention.

In a further sample embodiment, the conductive ink circuit may also include other conductive element components such as metal bands to link a series of conductive ink bands, or for the electrical connections. FIG. 4f shows a heater element 72 comprising a first layer of film 42a having a conductive ink 44 printed thereon and a metal layer 70 laid over the ink 44 on the first layer of film 42a. A second film 42b is laminated to retain the metal layer 70. Any conductive metals or alloys may be used, for example copper, gold and nickel chrome, or any other electrically conductive metal.

Heater Element Seventh Embodiment

Figure 4G:
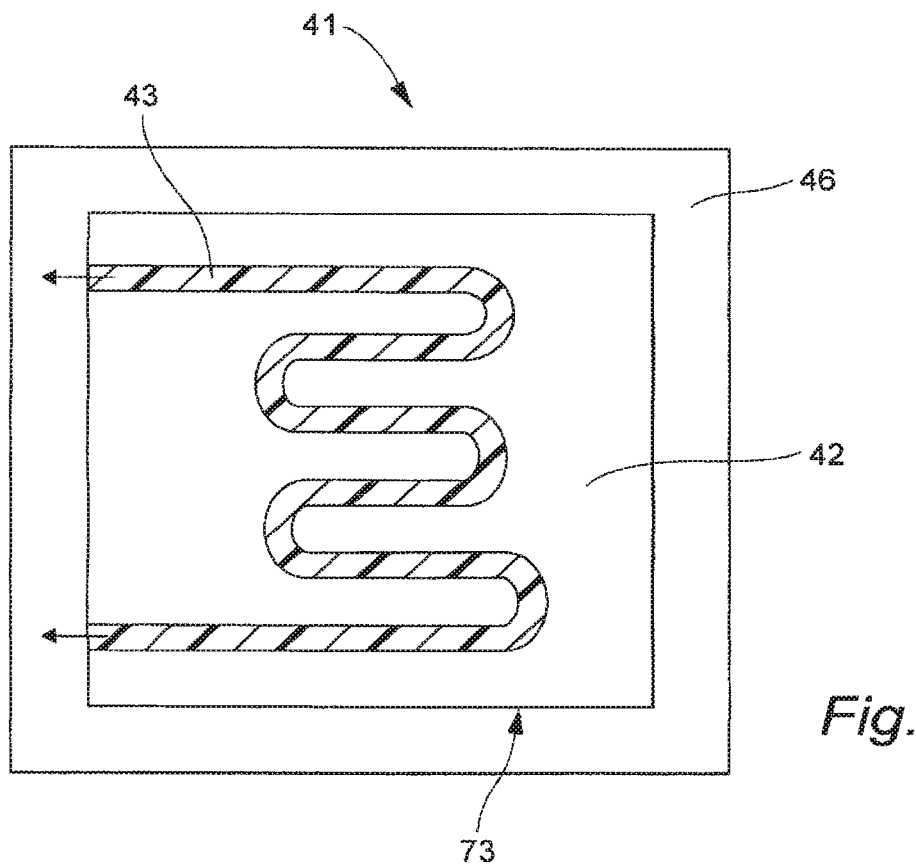
FIG. 4g schematically illustrates a heater element according to another sample embodiment of the invention.

Although various sample heater element embodiments have been described with respect to the use of conductive inks, it should be appreciated that the heater element circuit may be formed of, for example, conductive or resistive polymer film or an overmolded layer instead of, or in addition to, the conductive ink. For example, as shown in FIG. 4g, the heater element 41 may include a circuit formed of a conductive or resistive polymer film 43 that may be stamped to provide the circuit pattern. The conductive or resistive polymer film 43 circuit may be provided on a polymer film 42 to form a stamped film heater element 73.

Heater Element Eighth Embodiment

Figure 4H:
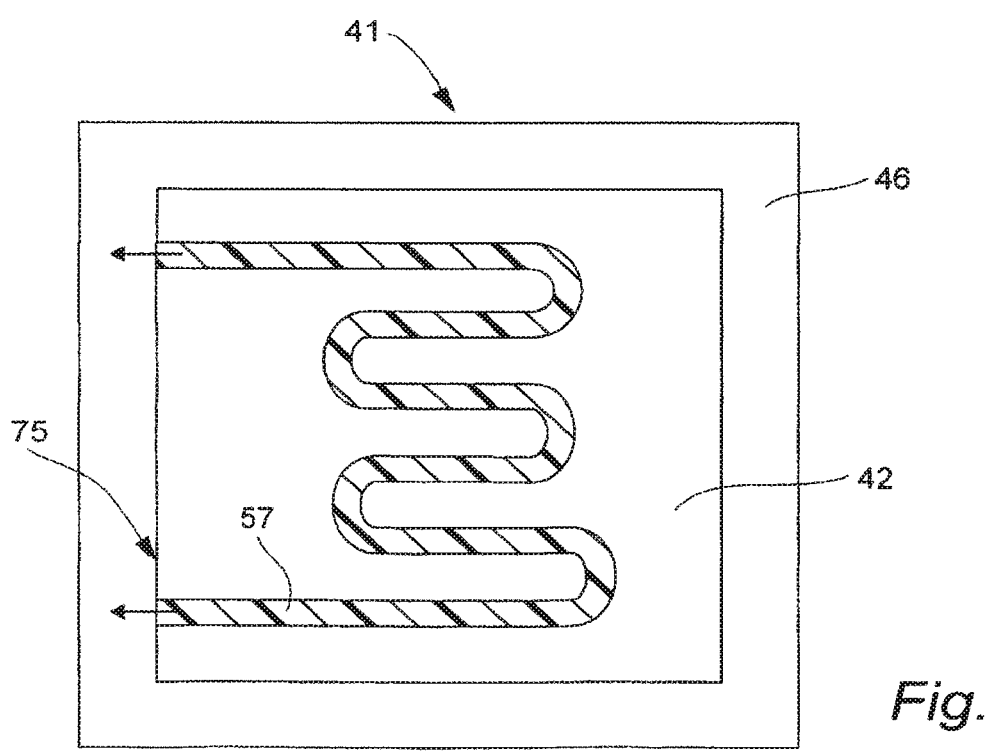
FIG. 4h schematically illustrates a heater element according to another sample embodiment of the invention.

As shown in FIG. 4h, the heater element circuit may be formed by overmolding 57 the pattern of the circuit onto the film 42 to form an overmolded film heater element 75. The overmold layer 57 may be formed of a resistive or conductive material.

Heater Element Ninth Embodiment

Figure 4I:
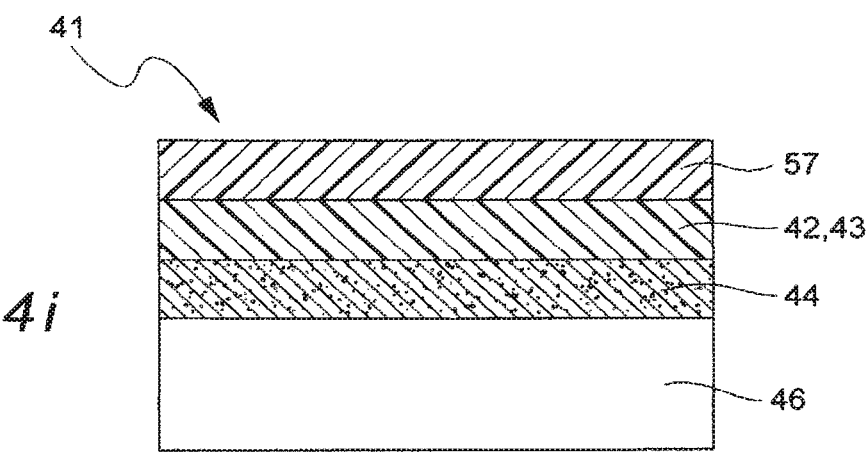
FIG. 4i schematically illustrates a heater element according to another sample embodiment of the invention.

Referring to FIG. 4i, heater element 41 and control circuit therefor may be formed by any combination of conductive ink 44, conductive or resistive polymer film 43, and/or overmolding 57. It should be further appreciated that the heater element 41 and control circuit may be used, for example, with the metal layer described above with respect to FIG. 4f. The heater element circuit and/or the control circuit may be formed of multiple layers of conductive ink, conductive or resistive polymer film(s), and/or overmolding to control the thermal properties.

Heater Element Tenth Embodiment

Figure 4J:
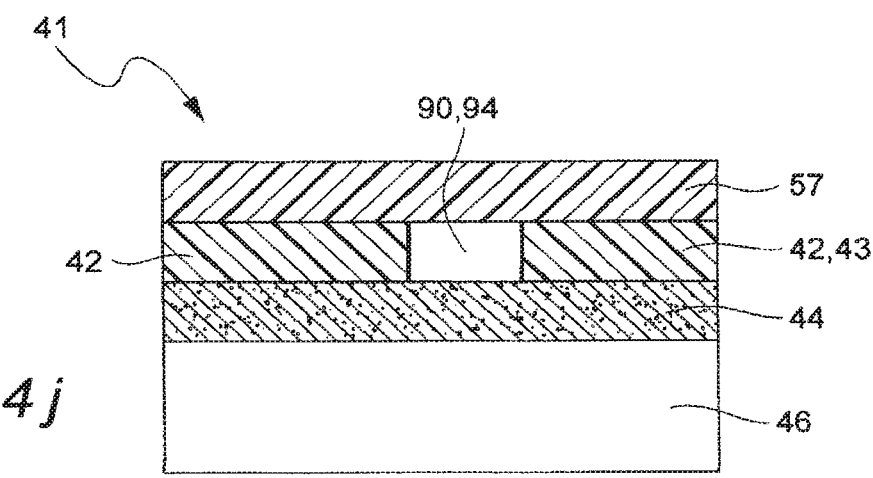
FIG. 4j schematically illustrates a heater element according to another sample embodiment of the invention.

Referring to FIG. 4j, the heater element circuit may be formed of conductive ink(s) 44, and a film or foil 43 may locate, connect, and/or thermally protect a thermal sensor 90, 94, e.g. a thermistor. The thermal sensor may then be overmolded 57 to control the thermal properties of the sensor, and/or to insulate the sensor from the water of a humidifier tub.

Heater Element Eleventh Embodiment

Figure 4K:
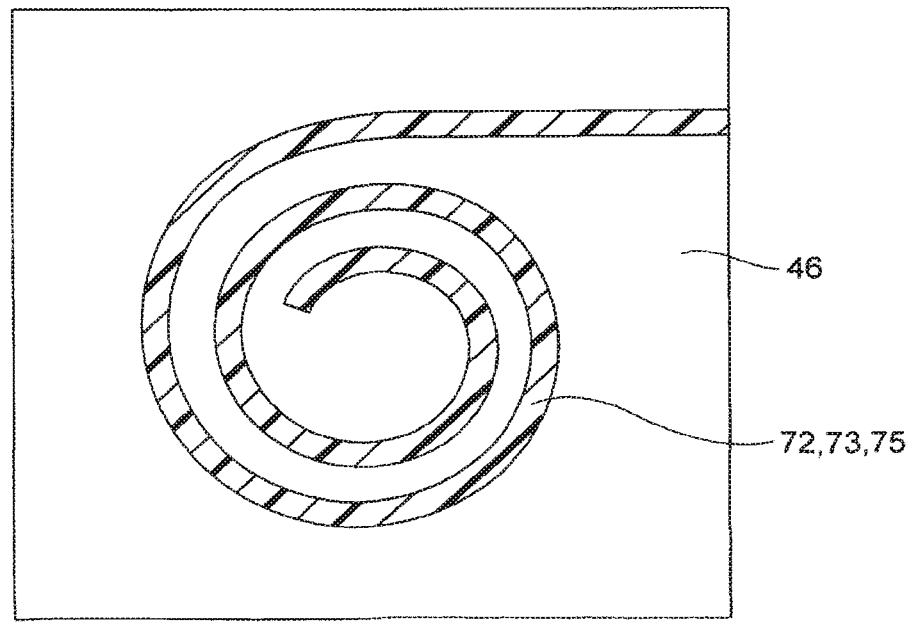
FIG. 4k schematically illustrates a heater element according to another sample embodiment of the invention.

As shown in FIG. 4k, the heater element may be either a printed film heater element 72, a stamped film heater element 73, and/or an overmolded heater element 75 and may be formed in a shape, for example a spiral, that is configured to cause differential heating to thereby cause water currents to form. For example, the heater element may be configured to create a swirling flow. As another example, the heater element may be formed with portions causing differential heating in areas of a humidifier where water flow may tend to be reduced, or stagnant, compared to other portions of the humidifier.

In the embodiments discussed above, any suitable molding resin may be used, including such resins as polycarbonate, polycarbonate ABS blends such as Astaloy™, polyethylene and polypropylene. The molded object 46 may be formed using extrusion molding or injection molding techniques or any other appropriate molding techniques. The molded object 46 comprising the in-mold heater 41 of the invention, including the printed film heater element 72, the stamped film heater element 73, and/or the overmolded heater element 75, may be made into any desired shape and may be used for a range of heating applications, for example, water baths, heaters, heating racks, syringe heaters, humidifiers, heated containers such as battery heaters and other suitably moldable objects and products.

Humidifier and Humidifier Tub First Embodiment

Figure 5A:
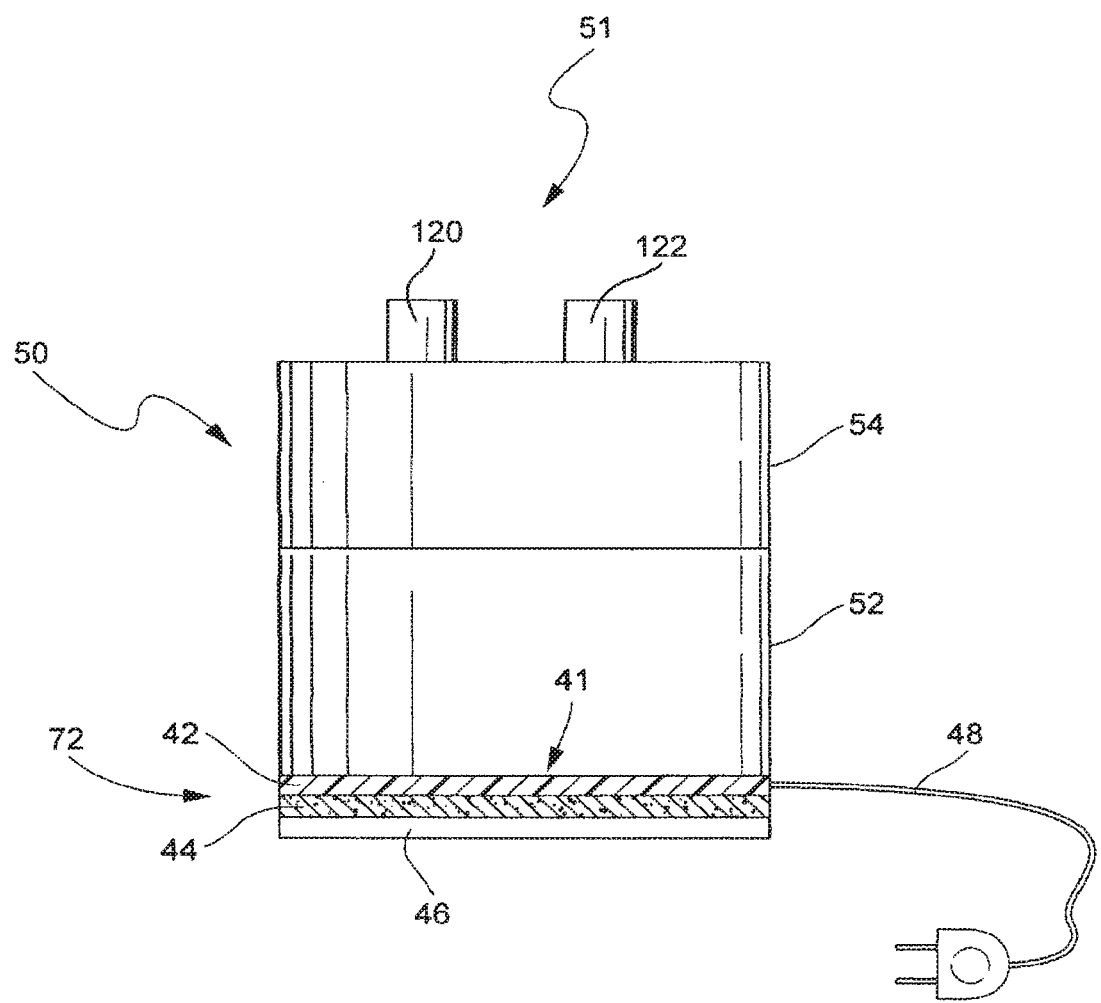
FIG. 5a schematically illustrates a humidifier according to a sample embodiment of the invention.

In one sample embodiment, the in-molded heater element 41 is formed within a humidifier device, for example in a respiratory humidifier device 51. FIG. 5a shows an embodiment of the in-mold heater element 41 of the invention used in a respiratory humidifier device 51. The conductive ink 44 is printed onto a film 42 and the subsequently formed printed ink film heater element 72 is molded into the base and/or sides of a humidifier tub 50 during the molding of the humidifier tub 50. In this embodiment the humidifier tub 50 comprises an upper portion 54 and a lower portion 52. The lower portion 52 comprises the in-mold heater element 41 at the base of the humidifier tub 50. However, it should be appreciated that the in-mold heater element 41 may be formed in any portion of the humidifier tub 50, for example in the sides, base, top or combinations thereof.

Humidifier and Humidifier Tub Second Embodiment

Figure 5B:
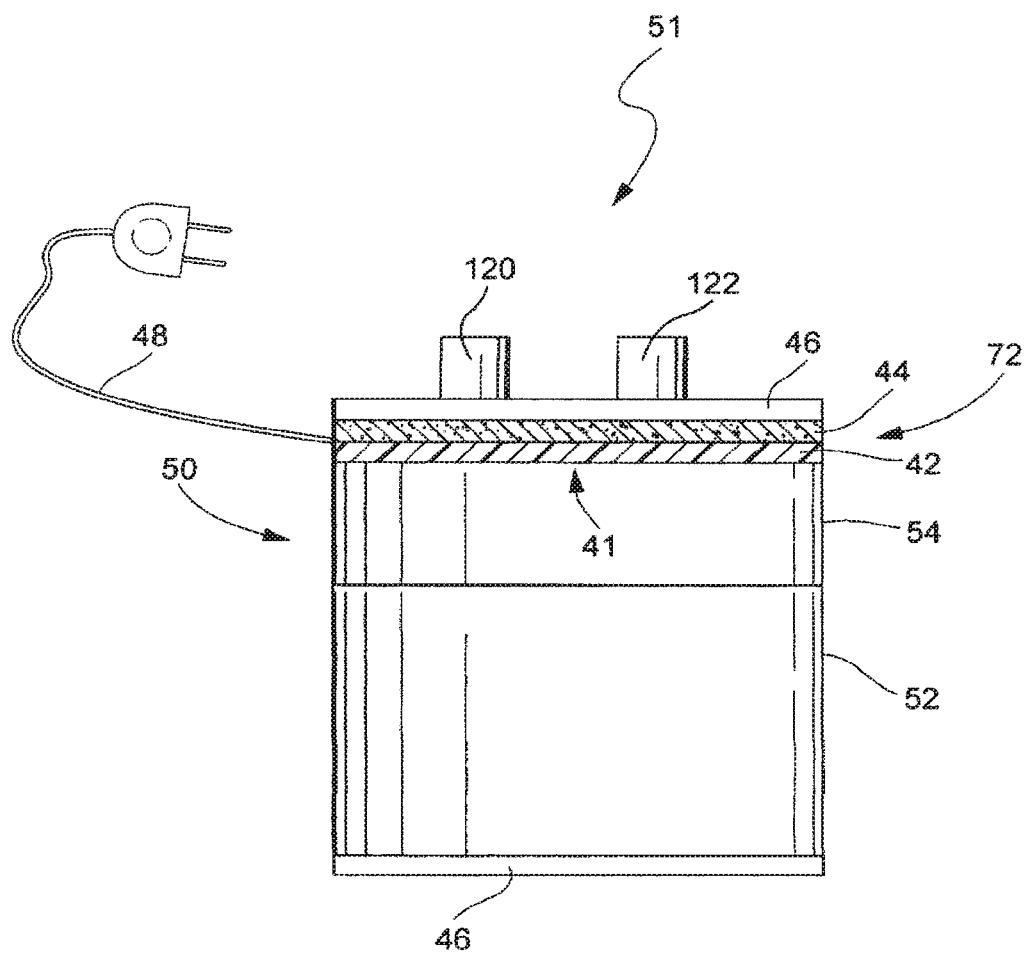
FIG. 5b schematically illustrates a humidifier according to a sample embodiment of the invention.

In another sample embodiment shown in FIG. 5b, an in-mold printed heater element 41 may be used to heat the air passing through the humidifier to enhance the moisture uptake by the air, or to adjust the temperature of the delivered air.

The upper portion 54 of the humidifier tub 50 comprises an air inlet 120 and an air outlet 122. However, the air inlet 120 or air outlet 122 or both may be located in the lower portion 52. The upper portion 54 may be formed as a removable lid to allow ease of cleaning and/or filling of the tub with water. Alternatively the upper portion 54 may be permanently fastened to the lower portion 52, for example by welding or gluing or any other techniques known to sealingly fasten components. A seal may be used between the upper portion 54 and the lower portion 52 to reduce the risk of water leakage. The joint between the upper portion 54 and the lower portion 52 may be located above the maximum water fill line of the humidifier tub 50 to reduce the likelihood of water leakages from the humidifier tub 50.

Electrical connections 48 provide power to the in-mold heater element 41 may be formed as part of the molding process within the humidifier tub, as described in more detail below. In a sample embodiment, the electrical connections 48 are attached to a power source and/or control source and are located above the maximum water fill line of the humidifier tub.

The molded respiratory humidifier may be configured as a stand-alone humidifier device or designed as an integrated device for attachment to a related product such as a PAP device, for example in a similar manner to the ResMed S8™ PAP device and the HumidAire™ 3i humidifier device. It should be appreciated that the in-mold heater elements may be molded into any appropriately molded object that requires a heater element.

Humidifier Tub Third Embodiment

Figure 5C:
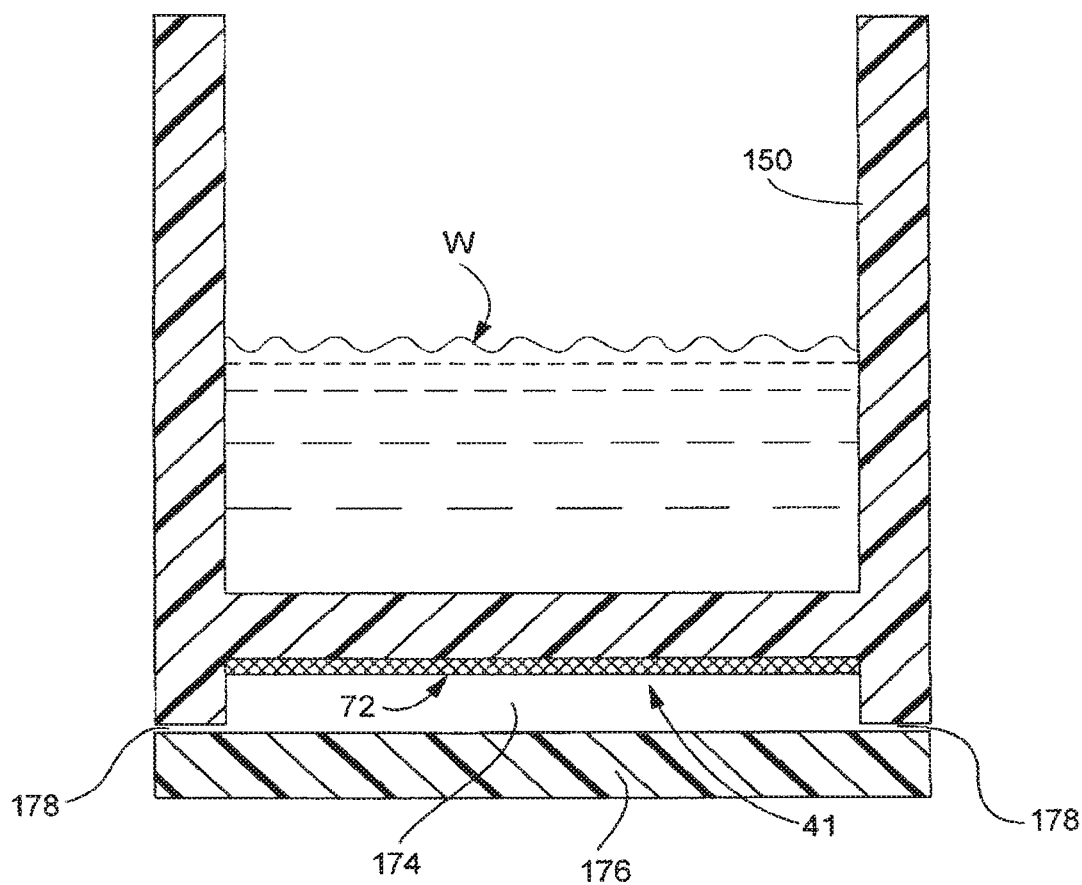
FIG. 5c schematically illustrates a humidifier according to a sample embodiment of the invention.

A sample humidifier tub embodiment is shown in FIG. 5c, in which the in-mold heater element 41 is not located within the inner surface of the humidifier tub 150 but on an exterior surface of the tub 150. In this embodiment, the in-mold heater element 41 may be molded into the exterior surface of the base of the tub 150 as described above or the heater element 41 may be a printed ink film heater element 72 in the form of a thick film heater that is attached to the base of the tub 150, for example using adhesives. To prevent access to the heater element 41, the tub 150 also comprises a base cover 176 that is attached to the base of the tub 150. In one embodiment the base cover 176 is sealed at contact points 178 to the allow ease of cleaning of the tub, for example in a dishwasher, without disturbing the heater element 41. A cavity 174 is formed between the heater element 41 and the base cover 176 to provide insulation. Insulating material may be inserted into the cavity 174 to prevent the heat transferring to the base cover 176. This embodiment allows easy access to electrical connections as they are provided on the exterior surface of the tub.

Humidifier Tub Fourth Embodiment

Figure 5D:
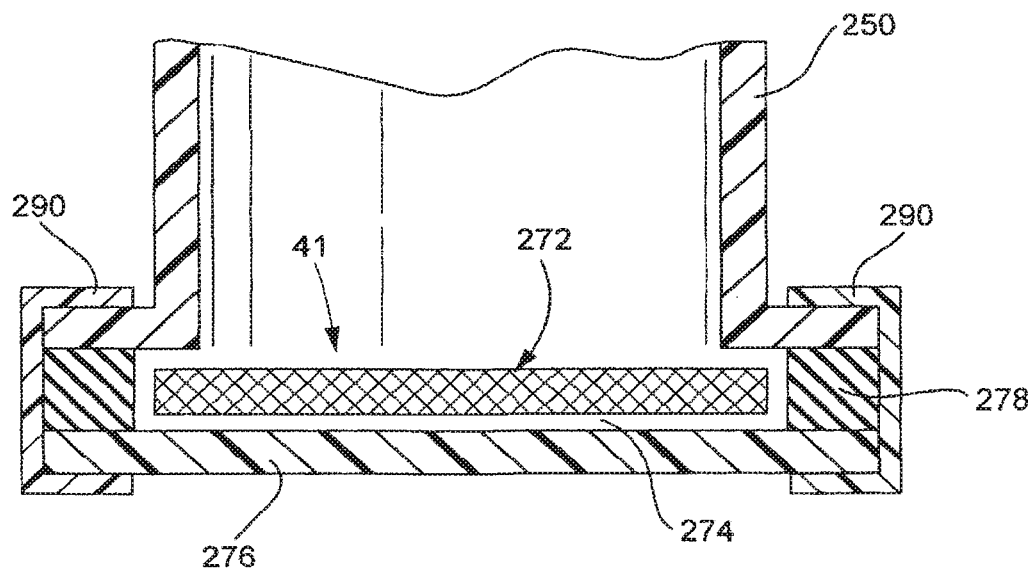
FIG. 5d schematically illustrates a humidifier according to a sample embodiment of the invention.

Another sample embodiment for a humidifier tub is shown in FIG. 5d. In this embodiment, the humidifier tub 250 is molded with an open base. A heater element 41 is located in the base of the humidifier tub 250 and a base cover 276 is attached to the base of the humidifier tub 250. The base cover 276 may be attached to the base of the humidifier tub 250 using a clamp 290 around the bottom perimeter. A seal 278 may be located between the humidifier tub 250 and the base cover 276 to prevent water leakage. The clamp 290 may permanently attach the base cover 276 to the humidifier tub 250, for example using an adhesive or rolled edge clamp. Alternatively, the clamp 290 may allow removal of the base cover 276 for cleaning or disinfecting purposes. In this embodiment, the clamp 290 may be in the form of a screw-on or press-fit arrangement or one or more clips. Furthermore, the clamp 290 may be formed as an integral part of the base cover 276, for example in the form of a screw-on base cover (not shown). The heater element 41 may be molded into the base cover 276 as described above or positioned in the base of the humidifier as a laminated heater element 272. The laminated heater element 272 may be attached to the base cover 276, for example using adhesives, or positioned above the base cover 276 to provide a cavity 274 under the laminated heater element 272. The laminated heater element 272 may provide the internal base of the humidifier tub 250 such that water in the tub cannot flow under the laminated heater element 272. In this embodiment, the cavity 274 under the heater element may provide an insulating layer to protect the base cover 276 from excess heat. Alternatively, the laminated heater element 272 may be positioned within the humidifier tub 250 to allow water to flow on both sides of the heater element 272 allowing heating of water on both sides of the heater element 272.

Electrical Connections

The in-mold heater element 41 requires electrical connections for operation of the heater element. Access to at least a portion of the in-molded heater element 41 or a connector attached to the heater element 41 is required at a suitable external position of the molded object (e.g. humidifier tub), to enable connection to a power supply unit. The electrical connector construction must establish an electrical connection between the heater element circuit, e.g. conductive ink, conductive or resistive polymer film, and/or overmolding, and an electrical contact.

In a sample embodiment, the electrical connections are molded into the object together with the heater element during the molding process. The electrical connections may be via a direct contact to the heater circuit or via connection to additional components, such as electrical wire or a metal contact. FIGS. 6a-6e show sample embodiments for the electrical connection. In all embodiments, the film 42 comprising the heater element circuit, e.g. printed conductive ink layer 44 of printed ink film heater element 72, is shown molded into the mold resin 46.

Electrical Connection First Embodiment

Figure 6A:
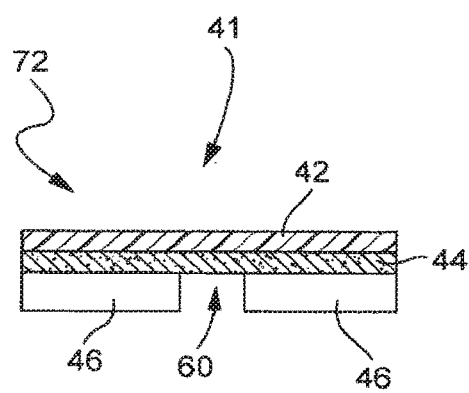
FIGS. 6a-6e schematically illustrate sample electrical connection embodiments of the invention.
Figure 6B:
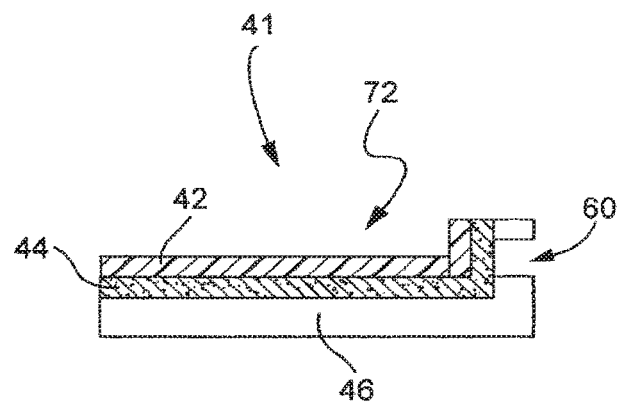
Figure 6C:
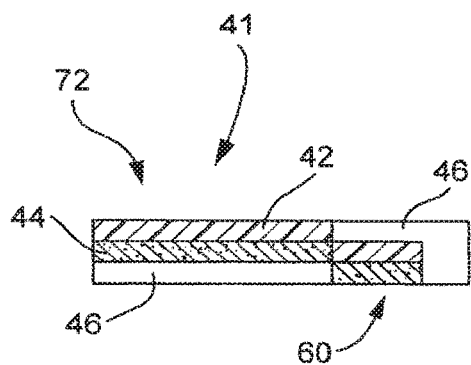

FIGS. 6a, 6b and 6c show examples of direct access 60 to the in-mold heater element 41, e.g. to the conductive ink 44, for direct contact to an electrical tab or connector, for example on a base unit or stand unit. The in-mold heater element 41 would be placed upon a complementary shaped tab or connector that may be connected to a power supply unit or electrical plug. In FIGS. 6a and 6b, the molded resin 46 is shaped to form the recess 60. In contrast, in FIG. 6c, the film 42 and the conductive ink 44 are exposed in a section of the mold such that no mold resin 46 is formed on a portion of the printed films.

Electrical Connection Second Embodiment

Figure 6D:
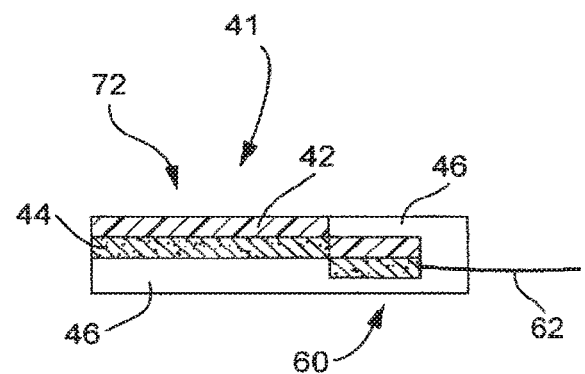
Figure 6E:
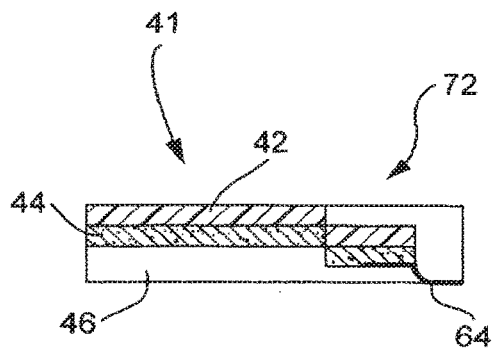

FIGS. 6d and 6e show the use of additional components for the electrical connection. FIG. 6d shows an electrical wire 62 fastened to the conductive ink 44 on the film 42. The electrical wire 62 may be fastened to the conductive ink 44 on the film 42 using techniques for fastening electrical connections, such as crimping or terminal blocks. Alternatively the fastened electrical wire 62 may include a rigid mechanical contact connector, for example a plug and socket type connector, such as a spade or bullet connector, for the connection to the conductive ink 44 on the film 42. The electrical wire 62 is fastened to the conductive ink 44 on the film 42 prior to the molding step with the mold resin. Thus, the electrical connection and electrical wire 62 is molded into the molded object together with the conductive ink 44 on the film 42. In another sample embodiment, illustrated in FIG. 6e, a conductive material 64, such as a metal contact, is fastened to the conductive ink 44 on the film 42 and the conductive material 64 is exposed on the outer surface of the molded object 46 to provide a direct electrical contact for a complementary electrical contact on a base or stand unit as described above for embodiments shown in FIGS. 6a-6c.

Humidifier Tub Fifth Embodiment

Figure 7A:
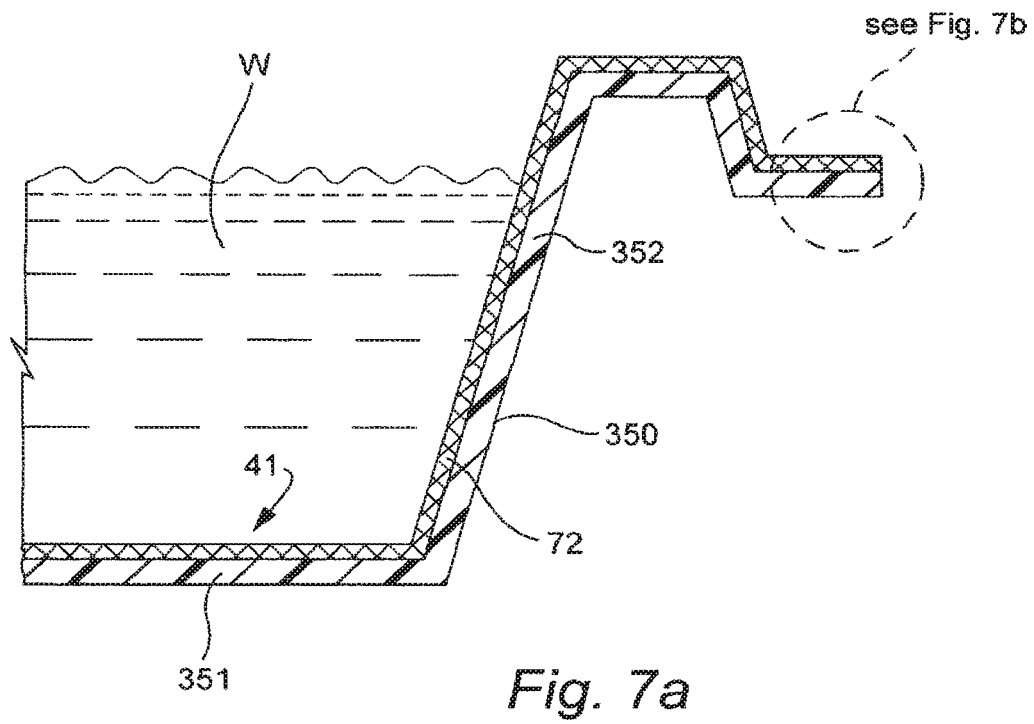
FIG. 7a schematically illustrates an arrangement for providing access for an electrical connection to the heater element molded into a humidifier according to a sample embodiment of the invention.
Figure 7B:
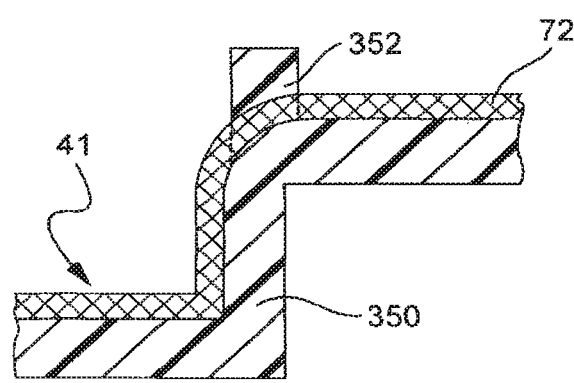
FIG. 7b schematically illustrates an arrangement for providing access for electrical connection to the heater element molded into a humidifier according to a sample embodiment of the invention.

FIG. 7a shows a humidifier tub 350 having a heater element 41 molded into the molded humidifier tub 350. The heater element 41 may be a printed ink film heater element 72 and be formed in the base 351 of the humidifier tub 350 and extend up at least one of the sidewalls 352. The sidewall 352 is molded with the heater element 72 to provide an external access for the electrical power and control connections above and/or away from the water W in the humidifier tub 350. FIG. 7b shows an alternative arrangement for providing access for the electrical connections where the heater element 72 is molded through the humidifier tub sidewall 352. The heater element 72 is shown on the upper surface of the sidewall 352, however it may also be provided on the lower surface.

Electrical Connection Third Embodiment

Figure 8:
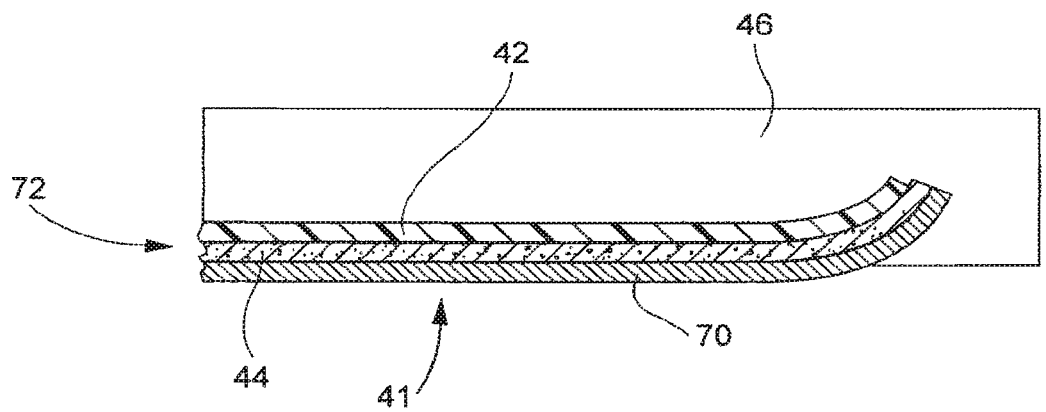
FIG. 8 schematically illustrates a heater element connector construction according to a sample embodiment of the invention.

The electrical connector for the molded object, e g humidifier tub, may be formed using features of the in-molded heater element 41, e.g. a printed ink film heater element 72. FIG. 8 shows an embodiment of a connector region. The connector region comprises a film 42 having the conductive ink layer 44 printed thereon and then having a further layer of metal 70 laid over the conductive ink layer 44. The molded resin 46 is added around the heater element 72 to form the molded object, e.g. humidifier tub. In this design, the molded resin 46 is formed on the internal surface of the object and the heater element 72 is on the external surface. The molded resin 46 provides the structural and physical support for the electrical connection. The molding may also be designed to provide guiding assistance when the heater element connector is engaged with the power supply connector. The metal layer 70 may be exposed on the external surface to provide a conductive contact connector.

Electrical Connection Fourth Embodiment

Figure 9A:
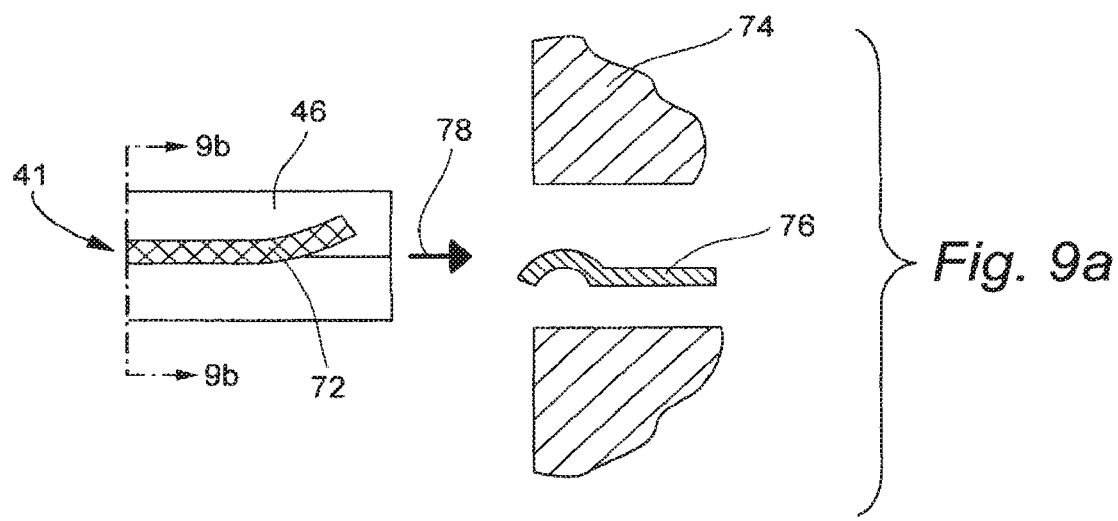
FIG. 9a schematically illustrates a sample embodiment of a mating arrangement for the molded heater element connector with a electrical supply unit.
Figure 9B:
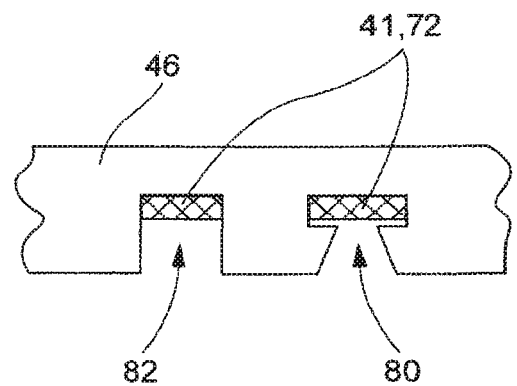

FIGS. 9a and 9b show an example of a mating connector design. The in-mold heater element 41, e.g. a printed ink film heater element 72 as described above, is formed within an exposed surface of the molded object 46. A complementary shaped connector portion is formed in the power supply unit 74. A spring contact 76 on the power supply unit 74 provides electrical connection to the exposed contact, e.g. metal layer 70, on the heater element 72 in the molded object 46 when the molded object 46 is inserted in direction 78 into the power supply unit 74. FIG. 9b shows a cross-section of the contact portions of the molded object. The shape of the molded connector region may be used to provide alignment for the connectors. The alignment portions may be formed in different shapes as indicated by 80 and 82.

Electrical Connection Fifth Embodiment

Figure 10:
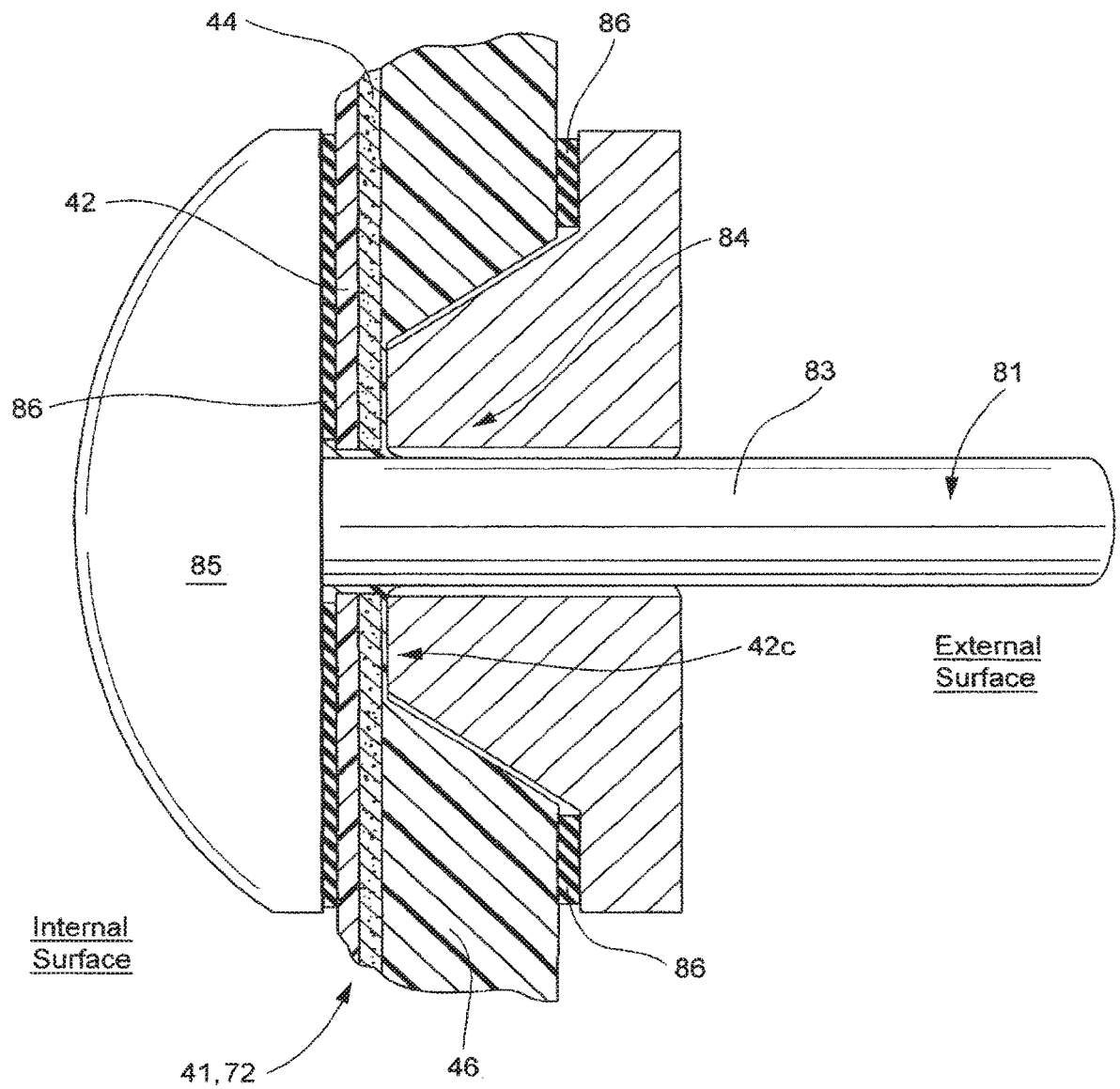
FIG. 10 schematically illustrates an electrical connector design according to another sample embodiment of the invention.

FIG. 10 shows another sample embodiment for the electrical connector construction to provide an electrical connection between the heater element and an electrical contact. In this embodiment, an electrical connector 81 having a pin-like structure 83 with a head portion 85 that is inserted through the molded object 46 and the in-mold heater element 41, e.g. a printed ink film heater element 72. The pin portion 83 of the electrical connector 81 is inserted from the interior of the molded object 46 until the head portion 85 is positioned against an internal surface of the molded object 46. In one embodiment, the electrical connector 81 is molded into the molded object 46 during manufacture. In an alternative embodiment, the electrical connector 81 is inserted after the molded object 46 is made. The electrical connector 81 contacts the heater element circuit, e.g. conductive ink layer 44, as it passes through the wall of the molded object 46. The molded object 46 may also be designed to expose the film 42 on the outer surface such that a portion of the conductive ink 44 is exposed on the external surface. A securement unit 84 is attached to the pin portion 83 of the electrical connector 81 to provide an increased electrical conductive interface 42a and to secure the electrical connector 81 in position. The securement unit 84 may be in the form of a screwed, riveted or glued adaptor, or the like. Seals 86 may be provided to ensure a secure and safe connection. The electrical connector may be above the water level in a humidifier tub.

Control System First Embodiment

Figure 11:
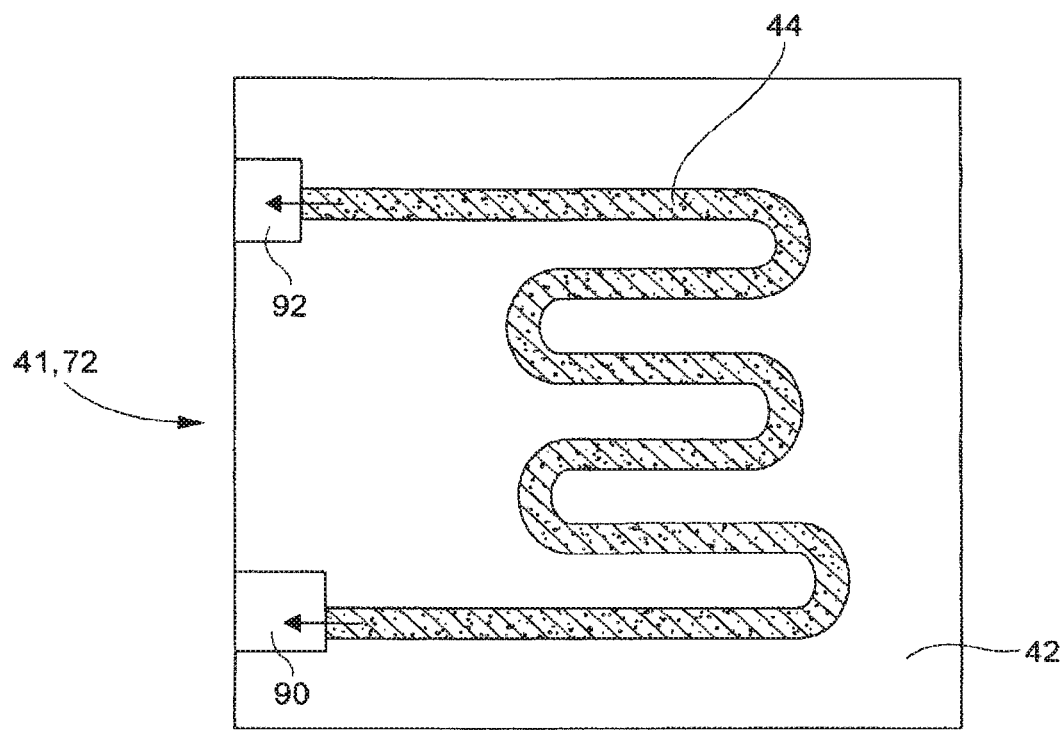
FIG. 11 schematically illustrates a heater element and control circuit according to another sample embodiment of the invention.

The level of heating by the in-mold heater elements may be controlled using a temperature sensor such as a thermistor or thermocouple. In a sample embodiment shown in FIG. 11, the in-mold heater 72 includes one or more thermistors 90, 92 electrically in series with the power supply and the printed conductive ink 44 on the film 42. Depending upon the application, a positive temperature coefficient (PTC) thermistor or a negative temperature coefficient (NTC) thermistor may be used to control the level of heating. For example, a PTC thermistor operates to decrease the heating power to the heater element as the temperature increases towards the desired temperature. A PTC thermistor may be used in a respiratory humidifier device.

Control System Second Embodiment

Figure 12:
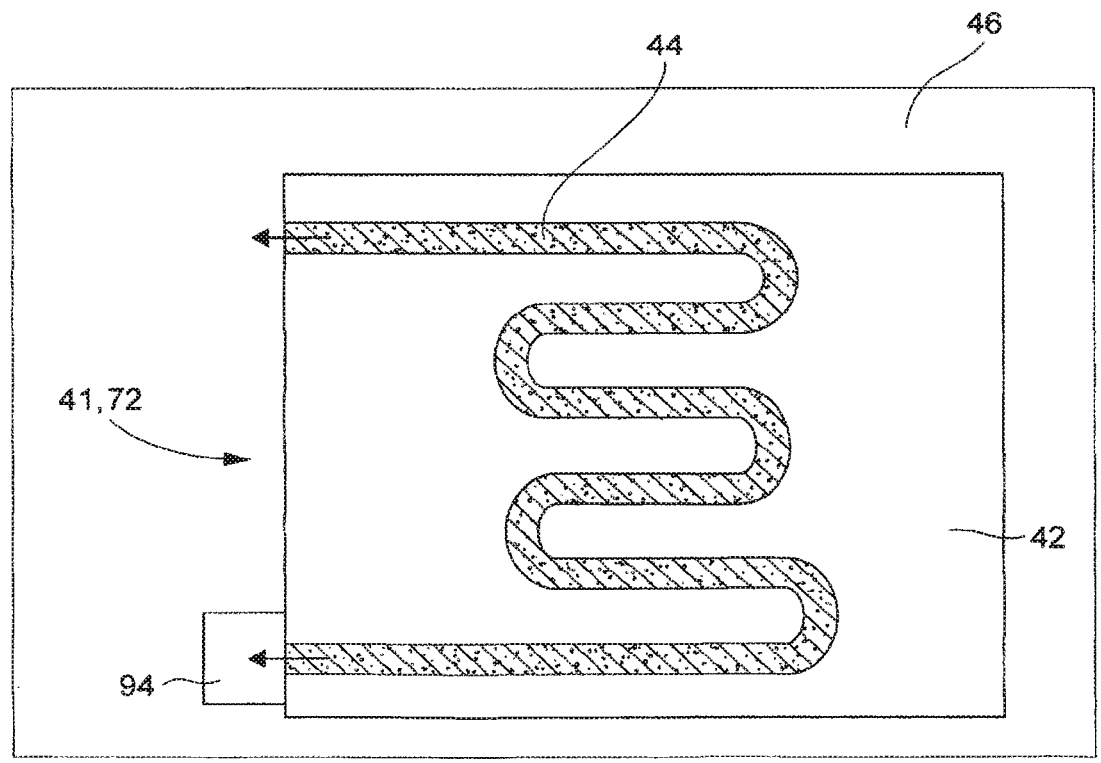
FIG. 12 schematically illustrates a heater element and control circuit according to another sample embodiment of the invention.

A temperature sensor 94, or thermistor, or conductive thermoplastic elastomer (PTC-TPE) with PTC electrical properties may be molded into the molded object 46 together with the heater element circuit, e.g. conductive ink 44, on the film 42, as shown in the sample embodiment depicted in FIG. 12.

Control System Third Embodiment

Figure 13:
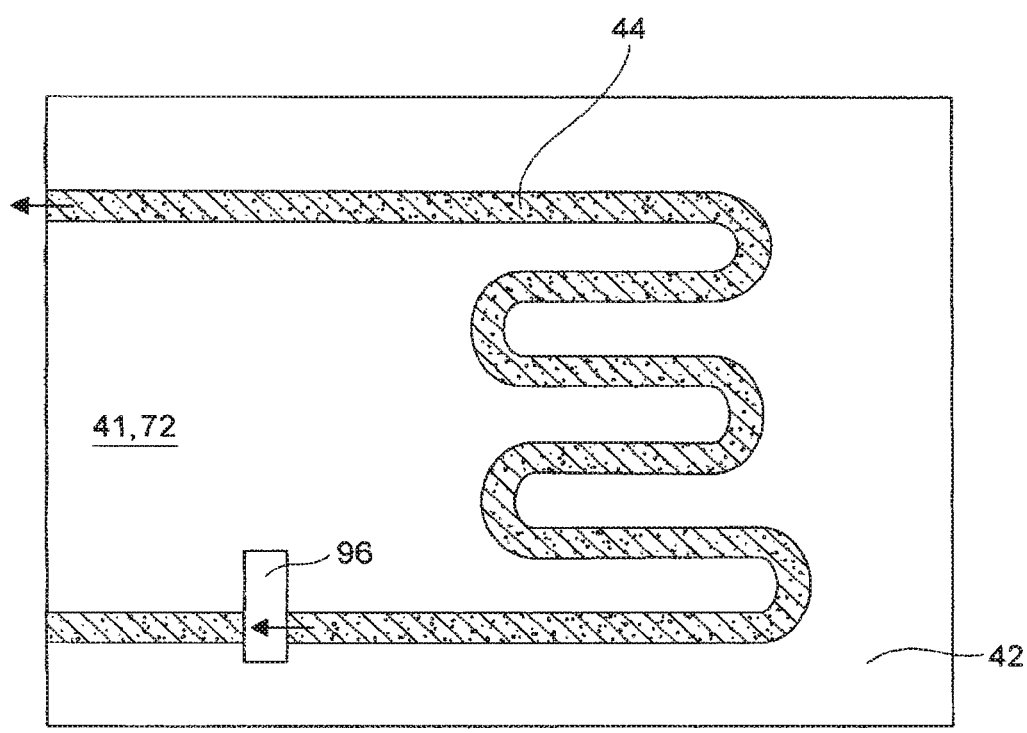
FIG. 13 schematically illustrates a heater element and control circuit according to another sample embodiment of the invention.

In another sample embodiment shown in FIG. 13, a thermal fuse 96 may be incorporated with the conductive ink 44 on the film 42 in a proximity close to the surface of the heater 72 to guard against overheating.

Control System Fourth Embodiment

Figure 14:
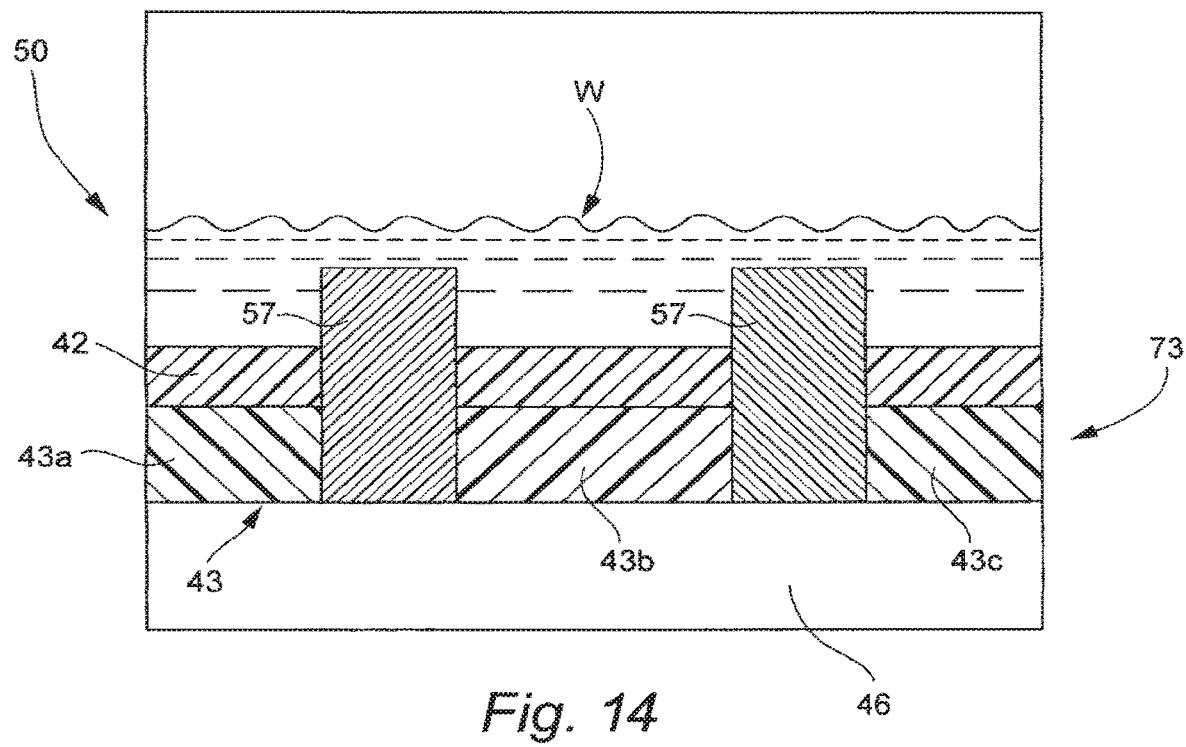
FIGS. 14 and 15 schematically illustrate a heater element and control circuit for use in a humidifier tub according to another sample embodiment of the invention.
Figure 15:
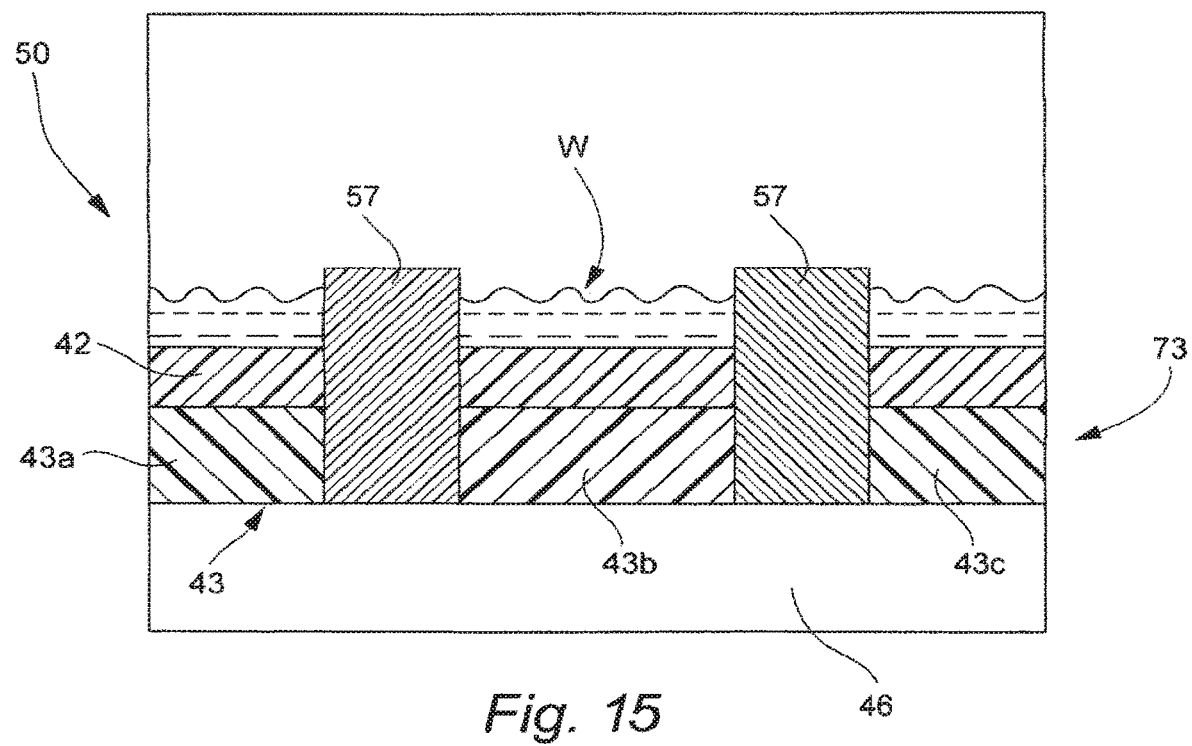

Referring to FIGS. 14 and 15, a humidifier tub 50 may include an in-mold heater element comprising, for example, a stamped film heater element 73 including a stamped resistive or conductive polymer film 43 and the polymer film 42. The tub 50 may also include an overmold material 57 that separates portions 43a, 43b, 43c of the polymer film 43. When the water level W is above the overmold material 57, the water forms a conductive circuit with the portions 43a, 43b, 43c of the polymer film 43, as shown in FIG. 14. When the water level W is below the overmold material 57, the conductive path between the portions 43a, 43b, 43c is broken. The polymer film 43 may thus be used as a water level sensor. For example, an amp meter may be connected to the polymer film 43. When the water level W falls below the overmold material 57, the conductive path is broken and the amp meter will detect the absence of current. It should be appreciated that the electrically conductive ink may be used instead of, or in addition to, the polymer film 43. It should also be appreciated that the polymer film 43 may be replaced by, for example, a conductive ink foil.

Control System Fifth Embodiment

Figure 16:
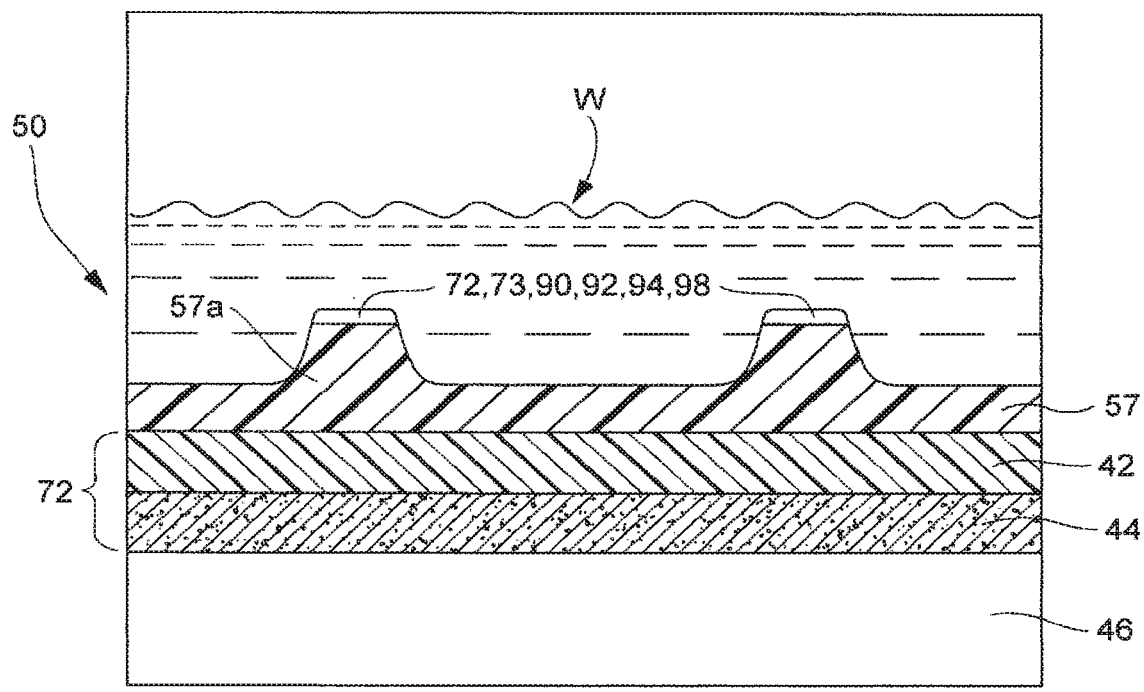
FIGS. 16 and 17 schematically illustrate a heater element and control circuit for use in humidifier tub according to another sample embodiment of the invention.
Figure 17:
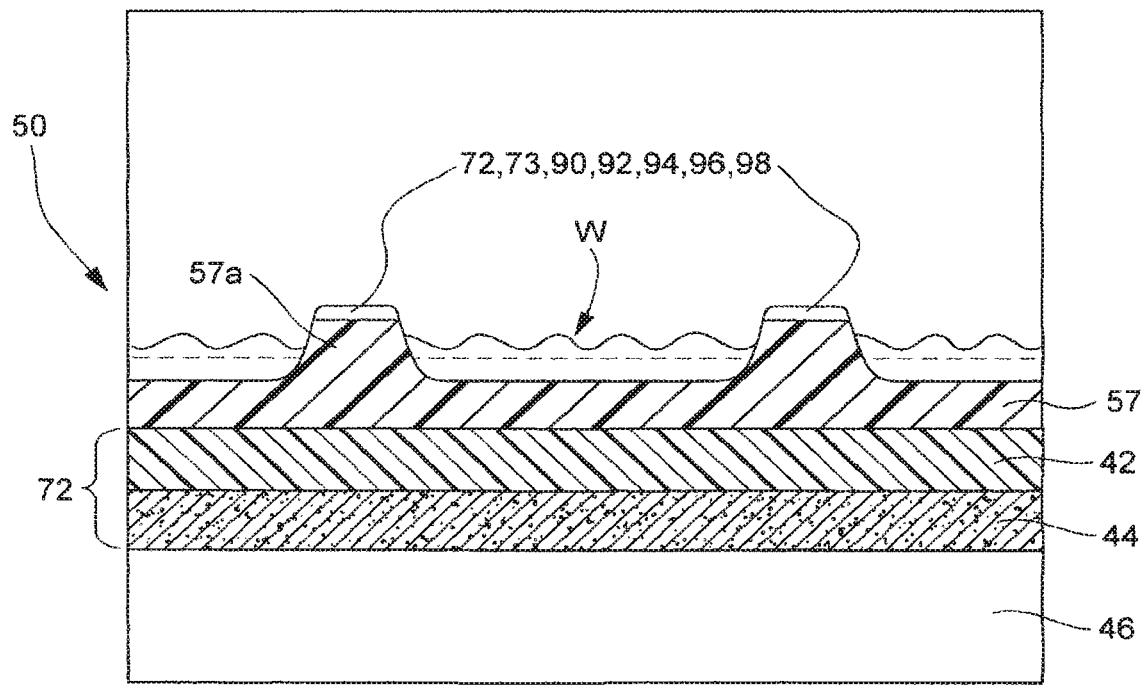

According to another sample embodiment shown in FIGS. 16 and 17, the humidifier tub 50 may include a printed ink film heater element 72 that comprises a conductive ink 44 and a polymer film 42. The humidifier tub 50 may also include an overmolded material 57 formed over the heater element 72. As shown in FIGS. 16 and 17, the overmolded material 57 may include a mound(s), or "volcano(es)", 57a that is formed above the remainder of the overmolded material 57. The mound 57a may include, for example, another heater, including another printed ink film heater 72 or a stamped film heater 73, thermistors 90 or 92, temperature sensors 94 or 98, and/or thermal fuse(s) 96. The additional heater element 72 or 73 may be electrically conductive when the water level W is above the overmolded mound(s) 57a, as shown in FIG. 16, and electrically non-conductive when the water level W is below the mound(s) 57a, as shown in FIG. 17. Thus, the mound(s) 57a may allow the additional heater element 72 or 73 to operate as a water level sensor as described above. Similarly, the thermistors 90 or 92 and/or the temperature sensors 94 or 98 may act as a water level sensor. For example, when the water level falls below the overmold mound(s) 57a, a large temperature differential may be sensed that indicates the water level has dropped below the mound(s) 57a.

Control System Sixth Embodiment

Figure 18:
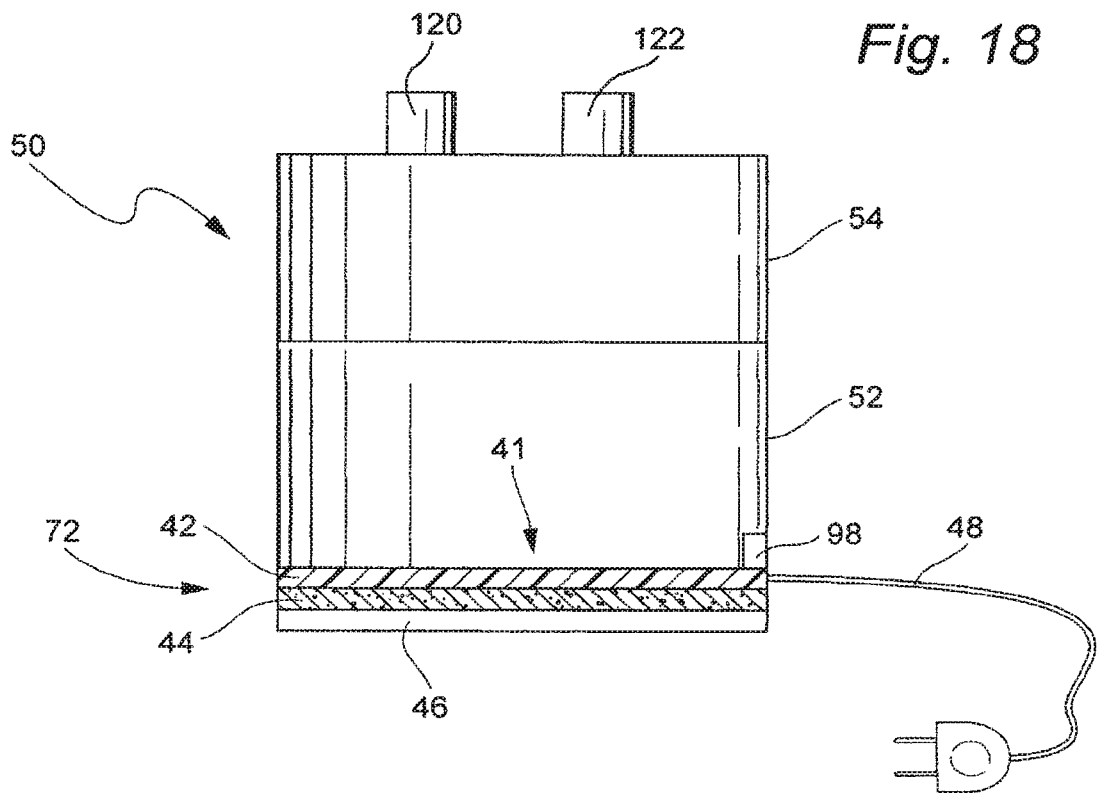
FIG. 18 schematically illustrates a heater element and control circuit for use in a humidifier tub according to another sample embodiment of the invention.

In another sample embodiment shown in FIG. 18, a temperature sensor 98 may be positioned adjacent the base of a humidifier tub and may be used to provide an indication of the water level. For example, if the water level is very low the heater element will heat up very rapidly. Other sensors, such as humidity sensors, may also be included within the molded object on the heater element to provide an indication of the level of humidification. Sensors may be loaded on to the heater element in contact with the conductive ink using conductive adhesives and covered with an epoxy for protection. Temperature sensors molded into different portions of a molded object may also provide an indication of the flow rate by detecting the temperature and rate between two temperature sensors.

Control System Seventh Embodiment

Figure 19:
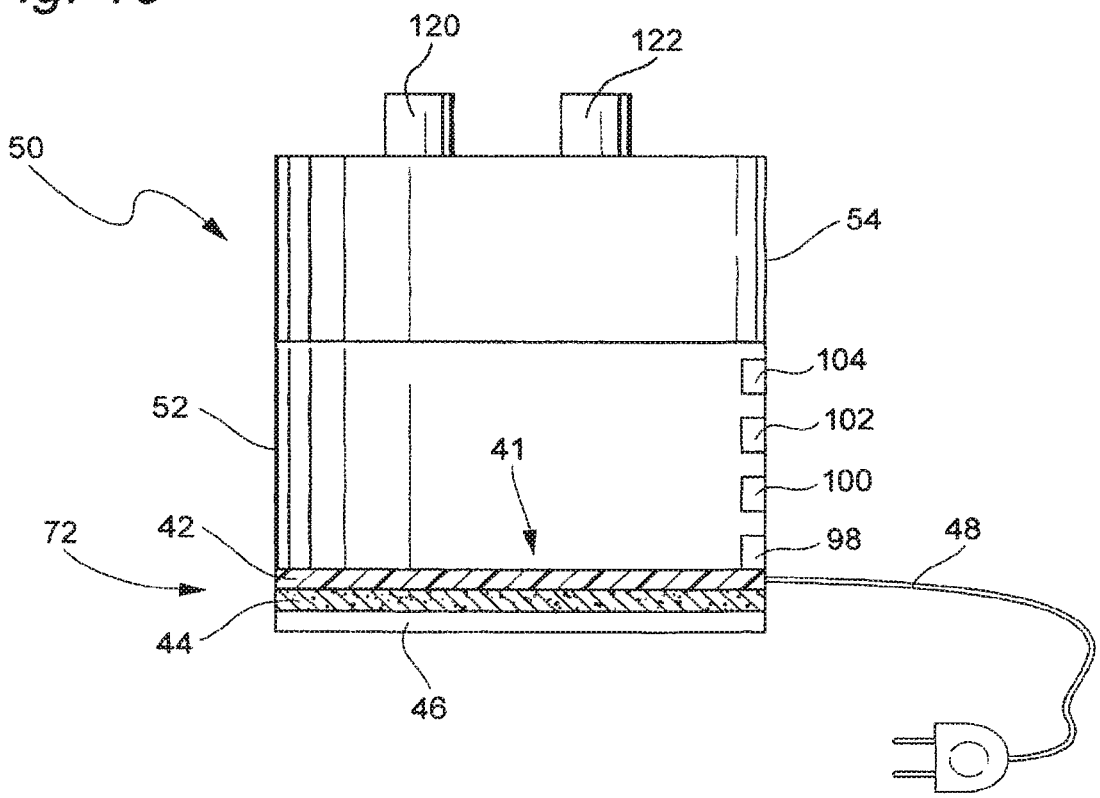
FIG. 19 schematically illustrates a heater element and control circuit for use in a humidifier tub according to another sample embodiment of the invention.

Referring to FIG. 19, a humidifier tub may comprise a lower portion 52 and an upper portion 54. The upper portion 54 may comprise an air inlet 120 and an air outlet 122. The lower portion 52 may comprise a printed film heater element 72, although it should be appreciated that the heater element may be a stamped film heater element or an overmolded film heater element as described above.

The lower portion 52 may comprise a plurality of temperature sensors 98, 100, 102, 104. As the water level in the lower portion 52 goes down, each sensor 104, 102, 100, 98 will be successively exposed to air flow through the humidifier. The change in the detected temperature, from water to air flow, provides an indication of the water level.

Control System Eighth Embodiment

Figure 20:
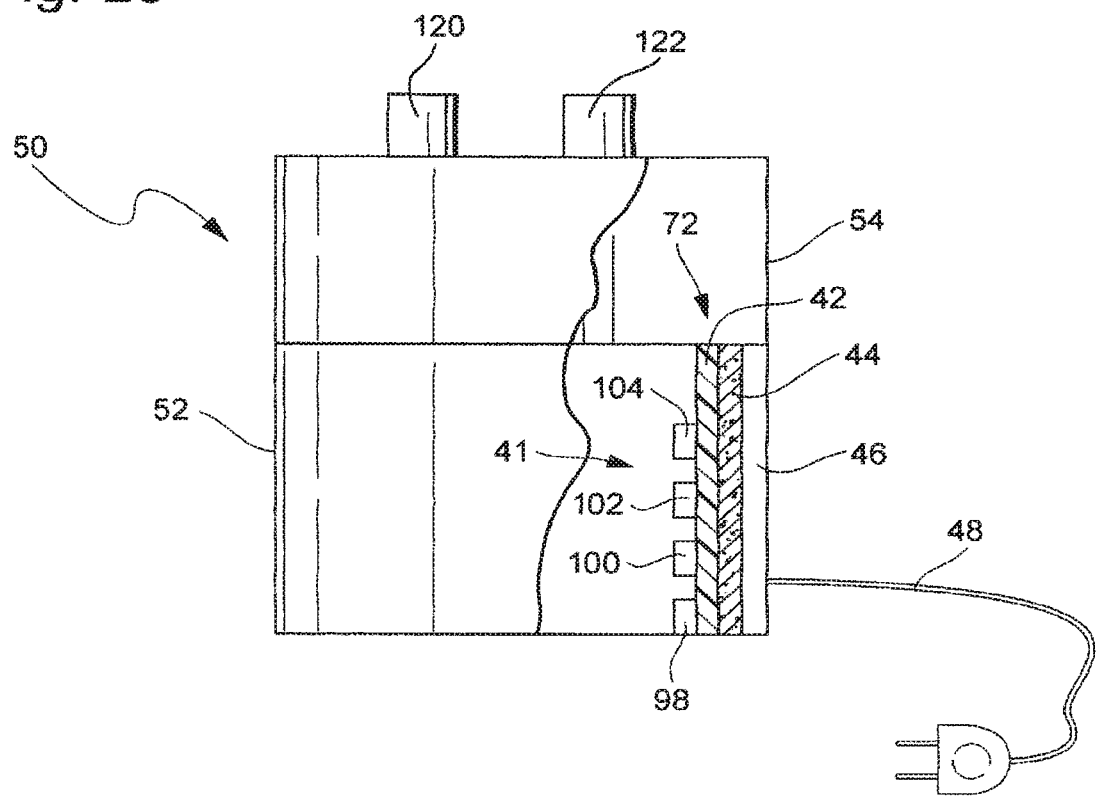
FIG. 20 schematically illustrates a heater element and control circuit for use in a humidifier tub according to another sample embodiment of the invention.

Referring to FIG. 20, the heater element 72 may extend along a side wall of the lower portion 52 of the humidifier tub 50 and include a plurality of sensors 98, 100, 102, 104 provided in the heater element to provide an indication of the water level. The heater element 72 will heat up more rapidly in areas not exposed to water in the lower portion 52 and the sensors in the areas of the heater element not exposed to water will indicate higher temperatures. It should also be appreciated that the circuit of the heater element 72 may also include, for example, a thermistor and/or a thermal fuse, as described in relation to other embodiments. It should be further appreciated that the heater element may be a stamped film heater element or overmolded film heater element as also described above.

Control System Ninth Embodiment

Figure 21:
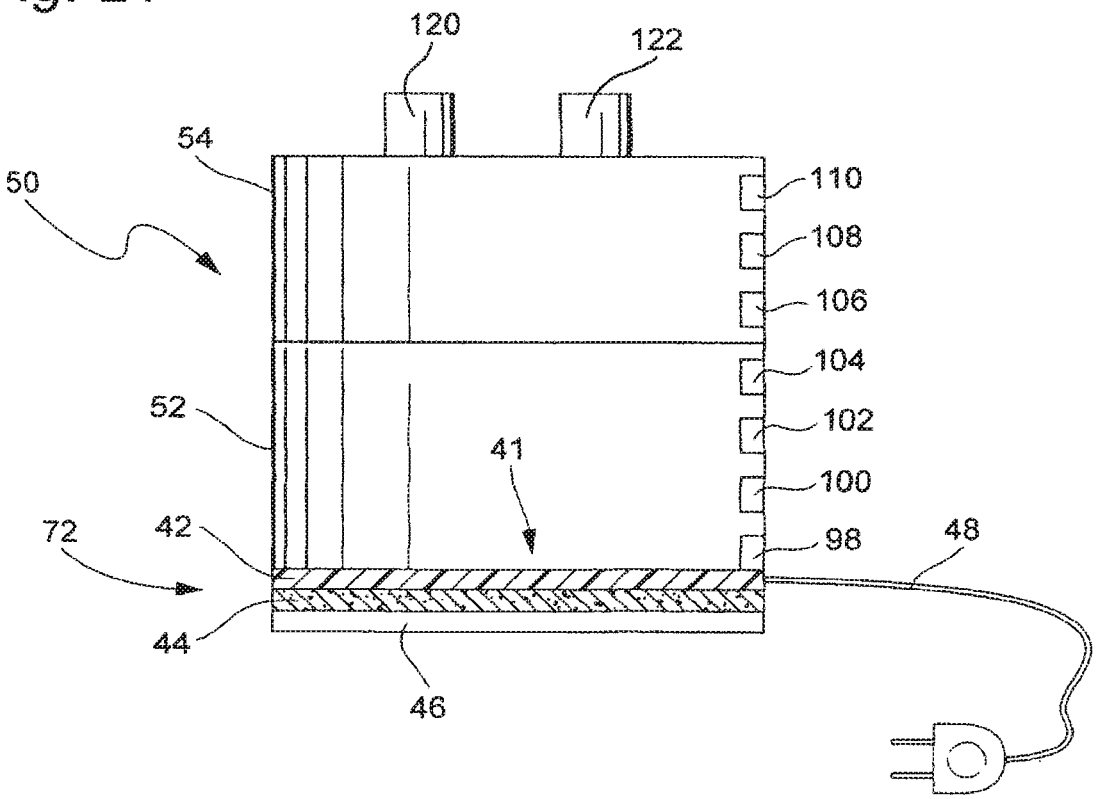
FIG. 21 schematically illustrates a heater element and control circuit for use in a humidifier tub according to another sample embodiment of the invention.

Referring to FIG. 21, the humidifier tub 50 may comprise the upper portion 54 and the lower portion 52. The upper portion may also comprise a thermal sensor, or sensors, 106, 108, 110. The thermal sensor(s) 106, 108, 110 may be placed above the water level, for example a maximum fill level defined in the lower portion 52, to detect a temperature of the air in the upper portion 54. If the air temperature exceeds a predetermined temperature, for example 40° C., the power provided to the heater element 72 may be controlled to lower the air temperature.

It should be appreciated that the heater element 72 may be provided in a base of the lower portion 52, as shown in FIG. 21, or the heater element 72 may be configured as in FIG. 20. It should further be appreciated that any positive number of temperature sensors 106, 108, 110 may be provided, and temperature sensors may be provided at multiple locations in the upper portion 54 of the humidifier tub 50. For example, a temperature sensor may be provided at the inlet 120 and/or the outlet 122 to provide control of the heater element. As the inlet air temperature changes, the power supplied to the heater element 72 may be controlled to maintain a predetermined temperature at the outlet.

Control System Variants

The film may also include a water level sensor. For example, a water level sensor including cathodic probes or a thermal gradient using temperature sensors, may be included in the molded object, e.g. humidifier tub. The sensors would rely on the thermal relationship between the heater and the water, and the ability to mold the shape of the molded object to accommodate the mechanical requirements of the humidifier. A humidity sensor(s), either an absolute and/or a relative humidity sensor may be provided in the humidifier to allow for control of the heater element. Such a control system is disclosed in, for example, U.S. Applications 61/034,318 and 61/042,112, filed Mar. 6, 2008 and Apr. 3, 2008, respectively, the entire contents of both being incorporated herein by reference.

The heaters may also be zoned. For example, the heaters may be provided on the film or overmolded material to include a water heating section and an air heating section. Each heater in each zone may include separate sensing, control, and/or thermal protection elements provided on the film. The zoning may also be horizontal for sensing and heating. Horizontal zoning would allow heating of the surface of the water only to improve warm up time and reduce energy losses.

In addition to temperature sensors molded into the molded object via the film or overmolded material, an electronic circuit, or circuits, may be provided on the film or overmolded material and molded into the molded object. For example, switching control elements may be provided on the film or overmolded material to recover heat losses that would normally be dissipated. The recovered heat may be used to heat the water in the humidifier chamber.

Power Supply

The power supply may be a stand alone power supply unit or incorporated within a supplementary device, such as PAP device that provides the power and electrical control systems for the device comprising the in-mold heater, such as an integrated humidifier device. Alternatively, the power supply unit forms a component of a humidifier device.

Advantages

The use of in-mold heater elements may provide a number of advantages over conventional heating technologies, including lower cost, ease of manufacture, reduced weight and increased efficiency. For example, the ability to mold the heater element within the molded object results in a reduction in the number of components and the time and complexity of assembly of the complete object. Hot plate and heat conductive plates are no longer required but are combined as the in-mold heater element performs the equivalent function. Such reductions may also lead to a significant cost savings. Furthermore, as the heater element may be included exactly where the heating is required there may be an increase in heating efficiency and response time. Molding the heater elements within the molded object also minimizes the chance of leakage in molded objects designed to hold fluids, such as humidifiers.

For a respiratory humidifier, the use of an in-mold heater element may have some significant benefits. For example, the humidifier may no longer require a cradle or chassis unit, which conventionally includes the hot plate and the structural features to secure the humidifier tub to ensure good thermal contact between the humidifier tub base and the hot plate. A humidifier tub base seal is no longer required and leakage problems should be reduced, or minimized These lead to component cost savings and simplified assembly making the humidifier unit less expensive to manufacture. The incorporation of the heater element within the molded humidifier tub can provide enhanced safety and protection against exposure to hot heating elements, especially when the humidifier is in use.

While the invention has been described in connection with what are presently considered to be the most practical embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has been described with particular application to humidification and patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A humidifier tub for a respiratory apparatus configured to humidify a pressurized flow of breathable gas and deliver the pressurized flow of humidified breathable gas to a patient's airways, the humidifier tub comprising:
 a container comprising a base and at least one side wall, the container being configured to contain pressurized breathable gas and a supply of liquid to be evaporated, the base and the at least one side wall being made of a first material;
 an air inlet configured to receive the pressurized flow of breathable gas from the respiratory apparatus and direct the pressurized flow of breathable gas into the container;
 an air outlet configured to discharge the pressurized flow of humidified breathable gas from the container;
 a heating element positioned on the base and/or the at least one side wall of the container below the air inlet and the air outlet; and
 a lining layer that lines an interior of the container and comprises at least a second material, the lining layer being located below the air inlet and/or the air outlet, wherein the second material of the lining layer covers the heating element and is configured to electrically isolate the heating element from the interior of the container, and
 wherein the second material is an electrical insulator and is different from the first material.

2. The humidifier tub of claim 1, wherein the heating element is provided on at least the base of the container.

3. The humidifier tub of claim 1, wherein the lining layer lines a substantial portion of an inner surface of the container.

4. The humidifier tub of claim 1, wherein the lining layer is molded over at least the heating element.

5. The humidifier tub of claim 4, wherein the lining layer is injection-molded.

6. The humidifier tub of claim 4, wherein the lining layer is molded over an inner surface of the at least one side wall of the container.

7. The humidifier tub of claim 1, wherein the lining layer covers the entire inner surface of the at least one side wall of the container.

8. The humidifier tub of claim 1, wherein the second material comprises any one of polyester, polyimide, polycarbonate, polypropylene and/or combinations thereof.

9. The humidifier tub of claim 1, wherein the lining layer is a film that has a thickness between 0.01 mm and 1 mm.

10. The humidifier tub of claim 9, wherein the lining layer is a film that has a thickness between 0.05 mm and 0.5 mm.

11. The humidifier tub of claim 1, wherein the heating element comprises a plug or connector to electrically connect to the heating element.

12. The humidifier tub of claim 1, further comprising one or a combination of the following: a temperature sensor, a humidity sensor, thermal overload protection, and a sensor configured to sense a level of the supply of liquid.

13. The humidifier tub of claim 1, wherein the container is injection-molded.

14. The humidifier tub of claim 1, further comprising a lid.

15. A method of manufacturing the humidifier tub according to claim 1, the method comprising:
 a) providing a mold for molding the container;
 b) positioning the heating element inside said mold; and
 c) molding the container made of the first material around said heating element, wherein the heating element is arranged on an inner surface of the container; and
 d) molding the second material over at least the heating element on the inner surface of the container in order to provide the lining layer.

16. The method of claim 15, wherein the heating element is arranged on at least the base of the container.

17. The method of claim 15, wherein molding the container made of the first material comprises injection-molding.

18. The method of claim 15, further comprising providing a plug or connector.

19. The method of claim 15, wherein the second material covers a portion of the inner surface of the at least one side wall of the container.

20. The humidifier tub of claim 1, wherein the lining layer is configured to interrupt an electrical signal indicative of a level of water in the humidifier tub upon the level of water falling below a predetermined threshold.

21. The humidifier tub of claim 1, wherein the lining layer is thinner than the base and the at least one side wall of the container.

22. The humidifier tub of claim 1, wherein the heating element is molded within the base and/or the at least one side wall of the container.

23. The humidifier tub of claim 1, wherein the air inlet and the air outlet are located on the at least one side wall of the container.

24. A respiratory system configured to deliver a pressurized flow of breathable gas to a patient's airways, the respiratory system comprising:
 a respiratory apparatus configured to pressurize a flow of breathable gas; and
 the humidifier tub of claim 1.

* * * * *